United States Patent [19]

Fujii et al.

[11] Patent Number: 4,598,077
[45] Date of Patent: Jul. 1, 1986

[54] AMIDINE DERIVATIVES AND CARDIOTONIC COMPOSITIONS

[75] Inventors: Setsuro Fujii, Toyonaka; Takuo Sato, Chiba; Hiroyuki Kawamura, Ichikawa; Takashi Yaegashi, Yachiyo; Masateru Kurumi, Narita; Takuo Aoyama, Sakura, all of Japan

[73] Assignee: Torii & Co. Ltd., Tokyo, Japan

[21] Appl. No.: 681,476

[22] Filed: Dec. 14, 1984

[30] Foreign Application Priority Data

Dec. 16, 1983 [JP] Japan .................. 58-237715

[51] Int. Cl.⁴ .................. A61K 31/155; A61K 31/535; C07C 123/00; C07D 295/14
[52] U.S. Cl. .................. 514/233; 514/236; 514/237; 514/255; 514/357; 514/399; 514/401; 514/517; 514/539; 514/554; 514/564; 514/565; 514/637; 544/162; 544/398; 546/278; 546/332; 548/335; 548/347; 548/355; 560/21; 560/34; 560/35; 562/435; 562/439; 562/440; 564/226; 564/246; 260/501.14
[58] Field of Search .................. 544/162, 398; 546/278, 546/332; 548/335, 347, 355; 560/21, 34, 35; 562/435, 439, 440; 564/226, 246; 260/501.14; 514/233, 236, 237, 255, 357, 399, 401, 517, 539, 554, 564, 565, 637

[56] References Cited

FOREIGN PATENT DOCUMENTS 1241832 6/1967 Fed. Rep. of Germany .

Primary Examiner—Robert W. Ramsuer
Attorney, Agent, or Firm—Beveridge, DeGrandi & Weilacher

[57] ABSTRACT

Amidine derivatives of the formula

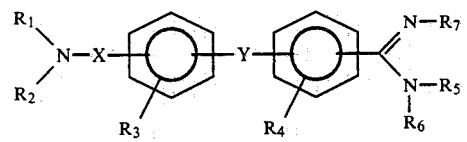

wherein $R_1$ and $R_2$, which may be the same or different, represent each a hydrogen atom or a lower alkyl group, or $R_1$ and $R_2$ together with an intermediary carbon atom and/or hetero atom may form a ring; X represents

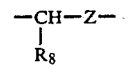

(wherein $R_8$ represents a hydrogen atom, a lower alkyl group, or —$CH_2COOR_9$, where $R_9$ represents a hydrogen atom or a lower alkyl group; Z represents a single bond, —$CH_2$—, —$CH_2CH_2$—, or —CH=CH—); $R_3$ represents a hydrogen or chlorine atom, methoxy group, nitro group, or amino group; Y represents —$CH_2CH_2$—, —CH=CH—, —$CH_2O$—, or —$OCH_2$—; $R_4$ represents a hydrogen atom, methoxy group, benzoyl group, nitro group, or amino group; and $R_5$, $R_6$ and $R_7$, which may be the same or different, represent each a hydrogen atom, lower alkyl group, cycloalkyl group, aralkyl group, substituted alkyl group, substituted aralkyl group, or amino group, or $R_5$ and $R_7$ may form a ring, or salts thereof have an excellent cardiotonic activity and can be used as cardiotonics.

2 Claims, No Drawings

AMIDINE DERIVATIVES AND CARDIOTONIC COMPOSITIONS

This invention relates to amidine derivatives or salts thereof and cardiotonics comprising said derivatives or salts thereof.

The amidine derivatives of this invention are represented by the general formula [I]:

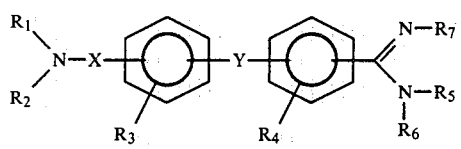

wherein $R_1$ and $R_2$, which may be the same or different, represent each a hydrogen atom or a lower alkyl group, or $R_1$ and $R_2$ together with an intermediary carbon atom and/or hetero atom may form a ring; X represents

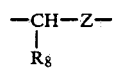

(wherein $R_8$ represents a hydrogen atom, a lower alkyl group, or —$CH_2COOR_9$, where $R_9$ represents a hydrogen atom or a lower alkyl group; Z represents a single bond, —$CH_2$—, —$CH_2CH_2$—, or —CH=CH—); $R_3$ represents a hydrogen or chlorine atom, methoxy group, nitro group, or amino group; Y represents —$CH_2CH_2$—, —CH=CH—, —$CH_2O$—, or —$OCH_2$—; $R_4$ represents present a hydrogen atom, methoxy group, benzoyl group, nitro group, or amino group; and $R_5$, $R_6$ and $R_7$, which may be the same or different, represent each a hydrogen atom, lower alkyl group, cycloalkyl group, aralkyl group, substituted alkyl group, substituted aralkyl group, or amino group, or $R_5$ and $R_7$ may form a ring.

The amidine derivatives represented by the formula [I] or salts thereof according to this invention have an excellent cardiotonic action and can be used as cardiotonics.

The amidine derivative or a salt thereof according to this invention has an ability to increase markedly the myocardial contractility (positive inotropic effect), while, on the other hand, its effect to increase the sinus rate is quite small, indicating a distinguished selectivity in favor of the myocardial contractility. Moreover, the positive inotropic effect of these compounds is characterized by being exhibited independent of the cardiac β-adrenoceptor activation, because said effect is entirely unaffected by propranolol, a β-adrenoceptor blocking agent. In an experiment on an anesthetized open-chest dog, it was also shown that the intravenous injection of the present compound increases the maximum rate of rise of left ventricular pressure (cardiac contractility) as well as the aortic flow. This suggests the usefulness of the present compound for the relief of heart failure.

In formula [I], $R_1$ and $R_2$, which may be the same or different, represent each a hydrogen atom or a lower alkyl group, preferably $R_1$ and $R_2$ are the same and represent a hydrogen atom, or $R_1$ and $R_2$ together with an intermediary carbon atom and/or a hetero atom may form a ring such as, for example,

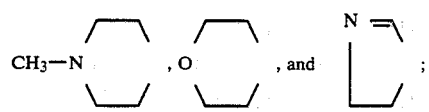

X represents

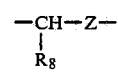

(wherein $R_8$ represents a hydrogen atom, a lower alkyl group, or —$CH_2COOR_9$, where $R_9$ represents a hydrogen atom or a lower alkyl group; Z represents a single bond, —$CH_2$—, —$CH_2CH_2$—, or —CH=CH—; X is preferably —$CH_2$—, —$CH_2$—CH=CH—, or —$CH_2CH_2CH_2$—); $R_3$ represents a hydrogen or chlorine atom, methoxy group, nitro group, or amino group; Y represents —$CH_2CH_2$—, —CH=CH—, —$CH_2O$—, or —$OCH_2$—; $R_4$ represents a hydrogen atom, methoxy group, benzoyl group, nitro group, or amino group; and $R_5$, $R_6$ and $R_7$, which may be the same or different, represent each a hydrogen atom, lower alkyl group, cycloalkyl group, aralkyl group, substituted alkyl group, substituted aralkyl group, or amino group, or $R_5$ and $R_7$ may form a ring.

Reaction schemes of the processes (a) to (g) for preparing the compounds of general formula [I] are shown below. In the formulas, "Halo" stands for halogen and "MZ" for

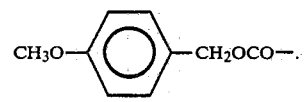

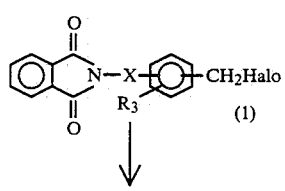

(a)

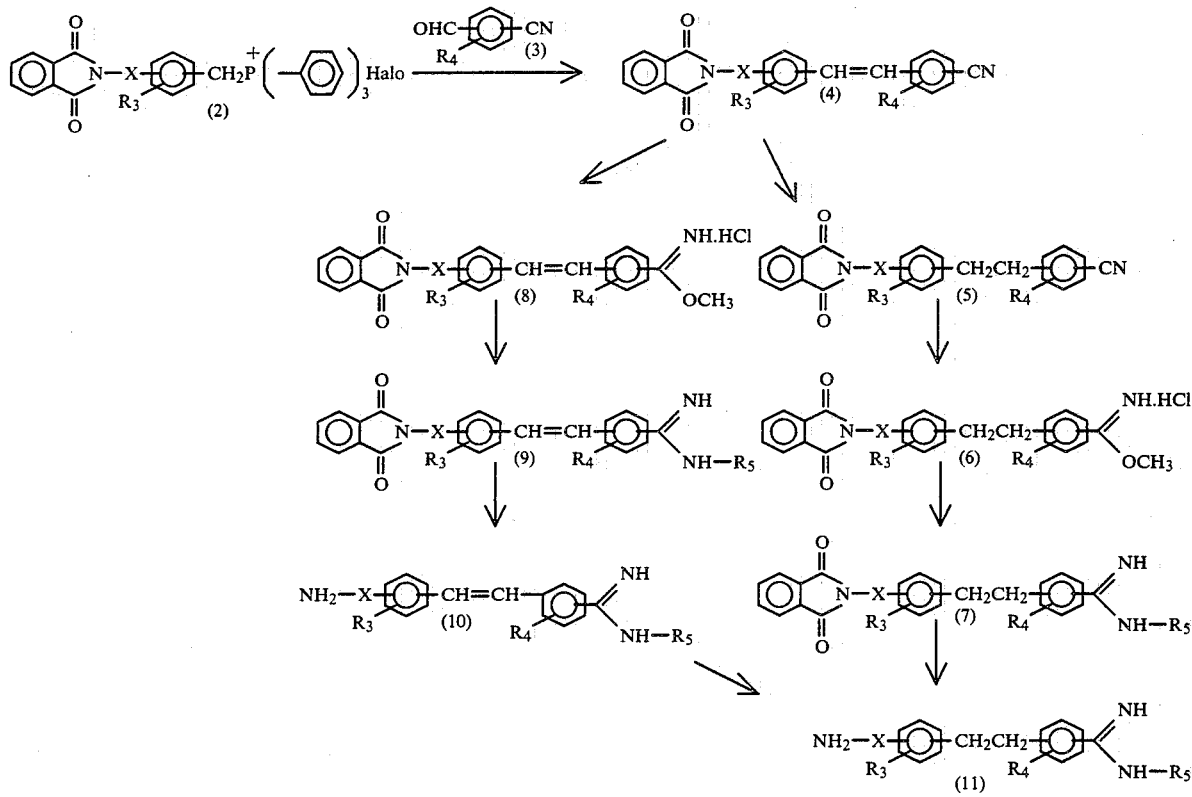
(b)
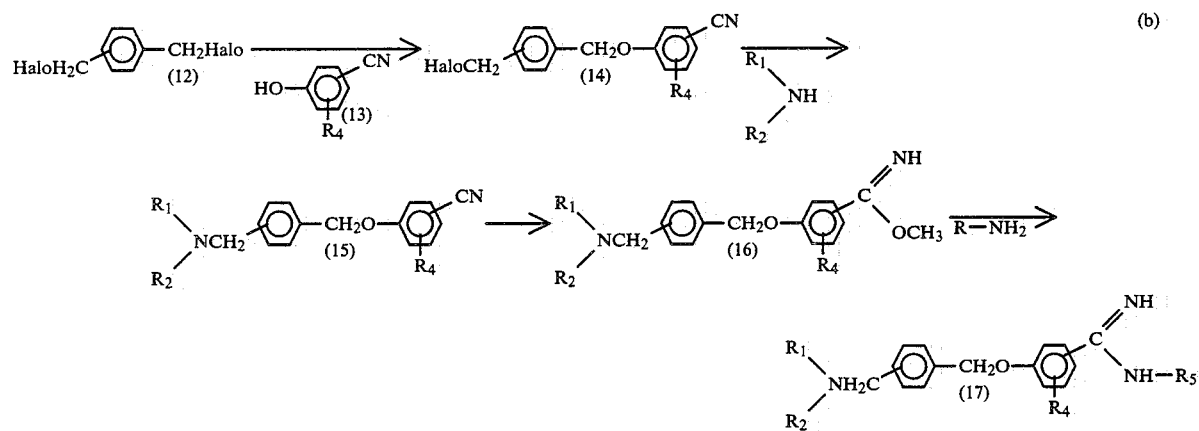
(c)
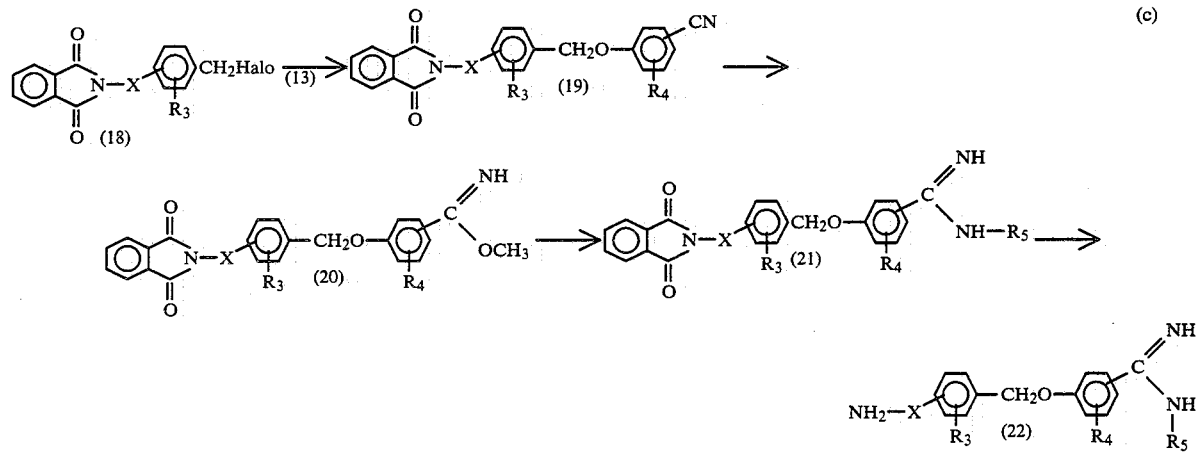

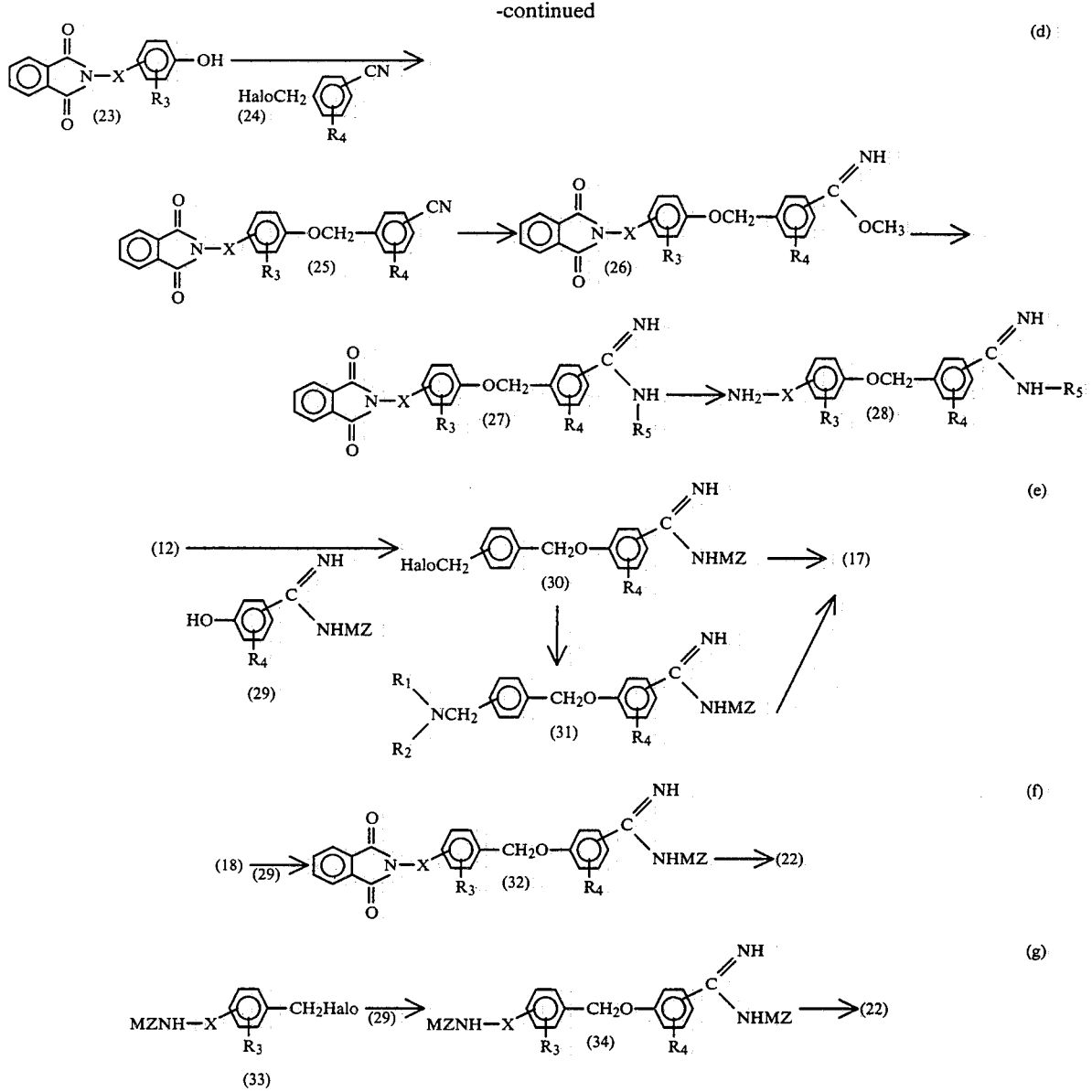

The procedures to carry out the processes (a) to (g) are as described below.

(a) In the step to obtain the phosphonium salt of formula (2), a halogen compound of general formula (1) is reacted with triphenylphosphine in a suitable solvent under reflux for 1 to 5 hours. As examples of the solvents, mention may be made of aromatic hydrocarbons such as benzene, toluene, and xylene. The reaction between the compound of formula (2) and the compound of formula (3) is carried out under usual Wittig reaction conditions to obtain the olefinic compound of formula (4). The bases used in the reaction include sodium methoxide, sodium ethoxide, and the like. Suitable solvents are methanol, ethanol, and the like. The reaction is conducted under a current of inert gases such as, for example, nitrogen and argon, generally at 20° to 100° C., preferably at room temperature and terminated in 2 to 15 hours. The reduction of the compound of formula (4) is performed under normal reduction conditions. Examples of suitable catalysts include metals such as palladium on carbon, platinum, and Raney nickel. The amount used of a catalyst is similar to that normally used in usual catalytic reduction. Suitable solvents include methanol, ethanol, and chloroform. This catalytic reduction is carried out preferably at room temperature under atmospheric pressure. The reaction to produce the compound of formula (6) from the compound of formula (5) is carried out under normal conditions for the Pinner reaction by adding dropwise over a period of 5 to 20 minutes at room temperature an anhydrous methanol solution containing 1 to 30 equivalents of hydrogen chloride into a solution of the compound of formula (5) in a solvent such as dichloromethane or chloroform. The reaction becomes complete in 3 to 15 hours. In a similar manner, the compound of formula (8) can also be derived from the compound of formula (4). The compound of formula (7) is obtained from the compound of formula (6) under the Pinner reaction conditions by reacting the latter compound with a primary amine. Examples of solvents used in the reaction are dichloromethane and chloroform. This reaction is carried out generally at 15° to 18° C., preferably at room temperature, and is completed in 1 to 15 hours. The removal of the protective group from the compound of formula (7) is performed normally in the presence of an acid to yield the compound of formula (11). Suitable acids used in the reaction are common inorganic acids, preferably concentrated hydrochloric acid and anhydrous hydrogen chloride. Solvents such as methanol and ethanol are preferred. This reaction is carried out generally at 80° to 120° C. and is completed in 6 to 30 hours. In a similar manner, the compound of formula (10) can be derived from the compound of formula (9). The reduction of the compound of formula (10) is performed under the conditions for common catalytic reduction. Examples of catalysts used in the reaction are metals such as palladium-carbon, platinum, and Raney nickel. These catalysts are used in amounts generally used in the catalytic reduction.

The solvents used in the reaction include methanol and ethanol. This catalytic reduction is carried out preferably at room temperature under atmospheric pressure.

(b) The benzyl ether of general formula (14) is synthesized by the method of Williamson from a dihalogenated xylene of formula (12) and a cyanophenol compound of formula (13). The resulting compound of formula (14) is dissolved in a suitable solvent (e.g. dimethylformamide, dimethyl sulfoxide, methanol, or ethanol) and reacted with various amine compounds represented by the formula

(e.g. ammonia, alkylamines, dialkylamines, and cyclic amines) to yield the compound of formula (15). An alcohol (methanol, ethanol, or the like) is added to the resulting compound of formula (15) in the presence of hydrogen chloride to form the imidate compound of formula (16) which is then condensed with various amines of the formula $R_5NH_2$ (ammonia, alkylamines, aralkylamines, and the like) to yield benzamidine derivatives of the formula (17) (Pinner amidine synthesis).

(c) The benzyl ether compound of the formula (19) is synthesized according to Williamson reaction from a halogenated benzyl compound of formula (18) bearing a substituent group, in which an amino group has been protected with a phthalyl group, and a compound of formula (13). The resulting benzyl ether compound is treated according to the method of Pinner as in (b) to yield the benzamidine compound of formula (21) via the compound of formula (20). The protective phthalyl group is removed by reacting the compound of formula (21) with various amine compounds (alkylamines, hydrazine, ammonia, and the like) in a suitable solvent (e.g. methanol, ethanol, dimethylformamide, and dimethyl sulfoxide) at a temperature from room temperature to boiling temperature, thereby to yield the benzamidine derivative of formula (22). Alternatively, the benzamidine derivative of formula (22) is obtained directly from the imidate compound of formula (20).

(d) In a manner similar to that in (c), a phenol compound of formula (23) bearing a substituent group, in which an amino group has been protected by a phthalyl group, and a cyano-halogenated benzyl compound of formula (24) are subjected successively to Williamson ether synthesis, Pinner amidine synthesis, and the reaction for removing phthalyl group, thereby to yield successively compounds of formulas (25), (26), (27) and finally the benzamidine derivative of formula (28).

(e) The compound of formula (12) and the amidinophenol compound of formula (29) having its amidino group protected by a 4-methoxybenzyl oxycarbonyl (hereinafter referred briefly to as MZ) group are subjected to Williamson ether synthesis to yield the benzyl ether compound of formula (30). The resulting compound of formula (30) is then reacted with various amine compounds (alkylamines, ammonia, and the like) in a suitable solvent (e.g. methanol, ethanol, dimethylformamide, and dimethyl sulfoxide, at a temperature from room temperature to boiling temperature, whereby both the conversion of halomethyl group into aminomethyl group and the exchange between the MZNH— group and the amino group are simultaneously effected. Alternatively, the compound of formula (30) is reacted with various amine compounds of the formula

[similar to those described in (b)] in a suitable solvent (similar to those described above) to form the aminomethyl compound of formula (31) which is then heated in acetic acid (anisole can be added thereto) under reflux to yield the benzamidine derivative of formula (17), wherein $R_5$ is hydrogen. The benzamidine derivative of formula (17) is obtained also by reacting the compound of formula (30) with various amine compounds (alkylamines, ammonia, hydrazine, and the like) in a suitable solvent (similar to those described above) at a temperature from room temperature to boiling temperature to effect the exchange between the MZNH— group and the amino compound.

(f) The compound of formula (18) and the compound of formula (29) are subjected to Williamson ether synthesis to yield the benzyl ether compound of formula (32) which is then treated as described previously to effect simultaneously both the removal of protective phthalyl group and the exchange between the MZNH— group and the amino group to yield the benzamidine derivative of formula (22).

(g) The halogenated benzyl compound of formula (33) bearing a substituent group, in which the amino group has been protected by MZ group, and the compound of formula (29) are subjected to Williamson ether synthesis to form the benzyl ether compound of formula (34). The resulting benzyl ether compound is removed of MZ group from the amidino group as described in (e), or is subjected to the exchange reaction between the MZNH— group and various amino compounds. The resulting compound is removed of the MZ group from the amino group by reacting with a mixture of an alcohol (methanol, ethanol, or the like) and anhydrous hydrogen chloride at a temperature from ice-cooled temperature to room temperature to yield the benzamidine derivative of formula (22).

In the above processes (a) to (g), when $R_4$ is a benzoyl group, the imino group can be converted into a carbonyl group in the final step by heating under reflux in a dilute hydrochloric acid (e.g. 3N hydrochloric acid) for 0.5 to 2 hours.

The compound of the present invention is administered either orally or parenterally. It is used as a remedy either alone or in mixtures with other drugs. Although can be administered in undiluted form, it is generally used in the form of pharmaceutical preparation. Examples of the forms include tablet, sugar-coated tablet, pill, granule, powder, capsule, syrup, and solution. The oral preparation can contain customary additives such as binder, excipient, lubricant, disintegrator, and humectant. The oral preparation can be in the form of aqueous or oily suspension, solution, emulsion, syrup, elixir, or in the form of dry syrup which is properly adjusted before use with water or other suitable solvents. Such liquid preparations may contain customary additives such as suspending agent, odorant, diluent, and emulsifier. For injection, an aqueous or oily suspension is used. The pharmaceutical preparation can be made in a manner customary in this field.

The present compound can be orally administered to mammals (including human patients) at a daily dose of 0.01 to 10 mg per kg of body weight. Such doses are presented merely by way of examples. The optimum dosage should be determined by taking into account of various factors such as the age, body weight, sex, and susceptibility of a particular patient, the mode, phase, and interval of administration, the rate of excretion, the combination with other drugs, and the degree of manifestation.

The invention is further illustrated below in detail with reference to Referential Examples and Examples. The Referential Examples show the preparative methods for the intermediates used in synthesizing the present compounds.

REFERENTIAL EXAMPLE 1

Into a solution of 10.0 g of 3-methoxy-4-methylbenzoic acid in 100 ml of dried tetrahydrofuran, while being cooled in ice and stirred under a nitrogen stream, was added dropwise over a period of 15 minutes 80 ml of a 1M solution of borane-tetrahydrofuran complex in tetrahydrofuran. The mixture was then stirred at room temperature for 3 hours. After addition of 10 ml of water, the reaction mixture was stripped of the solvent by distillation. The residue was dissolved in ether, washed with saturated aqueous sodium bicarbonate solution, then with saturated aqueous sodium chloride solution, dried over anhydrous magnesium sulfate, and stripped of the solvent by distillation to yield 7.6 g of 3-methoxy-4-methylbenzyl alcohol in the form of yellow oil.

PMR (CDCl$_3$) δ:2.15(1H, br), 2.20(3H, s), 3.82(3H, s), 4.62(2H, s), 6.67-7.30(3H, m).

REFERENTIAL EXAMPLE 2

To a solution of 7.6 g of 3-methoxy-4-methylbenzyl alcohol in 100 ml of dried ether, was added 4.0 g of pyridine. To the mixture, while being stirred at room temperature, was added dropwise 6.0 g of thionyl chloride. The resulting mixture was allowed to react for 30 minutes. The reaction mixture was washed with a 10% aqueous citric acid solution, then with saturated aqueous sodium chloride solution, dried over anhydrous magnesium sulfate, and stripped of the solvent to yield 8.2 g of a yellow liquid of 3-methoxy-4-methylbenzyl chloride.

IR$\nu_{max}^{heat}$ cm$^{-1}$: 2950, 1605, 1582, 1505, 1460, 1410.

REFERENTIAL EXAMPLE 3

A solution of 14.8 g of 3-chloro-4-methylbenzonitrile in 100 ml of acetic anhydride was catalytically reduced with 0.6 g of platinum oxide used as catalyst. The black sediment was removed by filtration and the filtrate was stripped of the solvent by distillation. The residue was fractionated and purified by silica gel column chromatography to collect 13.3 g of 4-acetamidomethyl-2-chlorotoluene; m.p. 99°–102° C.

REFERENTIAL EXAMPLE 4

To a mixture of 80 ml of concentrated hydrochloric acid and 8 ml of ethanol, was added 8.0 g of 4-acetamidomethyl-2-chlorotoluene. The stirred mixture was heated overnight under reflux. The solvent was removed by distillation and the residue was washed out with acetone to yield 7.7 g of 4-aminomethyl-2-chlorotoluene hydrochloride; m.p. ≦242° C.

REFERENTIAL EXAMPLE 5

To 100 ml of dried toluene, were added 7.7 g of 4-aminomethyl-2-chlorotoluene hydrochloride, 6.0 g of phthalic anhydride, and 6.1 ml of triethylamine. The mixture was heated under reflux for 3 hours, while removing the liberated water. The reaction mixture was washed with a 5% aqueous hydrochloric acid solution, then with saturated aqueous sodium chloride solution, dried over anhydrous magnesium sulfate, and freed from the solvent by distillation. The residue was recrystallized from methanol to yield 9.4 g of colorless granular crystals of 2-chloro-4-phthalimidomethyltoluene; m.p. 122.5°–123.5° C.

REFERENTIAL EXAMPLE 6

To 75 g of potassium phthalimide, were added 75 g of α-bromo-p-xylene and 500 ml of dimethylformamide (DMF). The mixture was stirred at 100° to 110° C. for 15 hours. After cooling, the insolubles were removed by filtration and the filtrate was concentrated under reduced pressure. The residue was recrystallized from 500 ml of methanol to yield 90 g of colorless needle crystals of 4-phthalimidomethyltoluene; m.p. 120°–121° C.

In a similar manner, the following compounds were obtained:
3-Phthalimidomethyltoluene, m.p. 115°–117° C.
2-Methoxy-4-phthalimidomethyltoluene, m.p. 115.5°–117° C.
2-Nitro-4-phthalimidomethyltoluene, m.p. 158°–161° C.

REFERENTIAL EXAMPLE 7

Twenty grams of 4-(1-aminoethyl)toluene were obtained from 25 g of 4-methylacetophenone by Leuckart reaction (Org. Synth., Coll. Vol. 2, 503).

IR $\nu_{max}^{liq.film}$ cm$^{-1}$: 3000, 2950, 2900, 2850, 1570, 1510.

A mixture of 9.2 g of 4-(1-aminoethyl)toluene and 10 g of phthalic anhydride was stirred at 145° to 150° C. for 30 minutes. The reaction mixture was purified by silica gel column chromatography (eluted with benzene) to yield 10 g of 4-(1-phthalimidoethyl)toluene; m.p. 65°–66° C.

REFERENTIAL EXAMPLE 8

To 10 ml of p-tolualdehyde, were added 180 ml of ethanol, 9.8 g of malonic acid, and 15.8 g of ammonium acetate. The mixture was refluxed for 5 hours. After cooling, the insolubles were removed by filtration.

After addition of 100 ml of water, the filtrate was adjusted to pH 7.0 with 1N hydrochloric acid, and the precipitated crystals were collected by filtration to yield 5.4 g of β-amino-β-(4-methylphenyl)propionic acid; m.p. 228°–229° C.

REFERENTIAL EXAMPLE 9

To 5.4 g of β-amino-β-(4-methylphenhl)propionic acid, was added 50 ml of anhydrous methanol. Into the mixture, was introduced with stirring anhydrous hydrogen chloride until saturation was reached. The mixture was then stirred at room temperature for 15 hours. After evaporation of the solution under reduced pressure, 50 ml of ether was added to the residue, and the precipitated crystals were collected by filtration. The crystals were thoroughly washed with ether to yield 4.5 g of methyl β-amino-β-(4-methylphenyl)propionate hydrochloride; m.p. 148°–150° C.

REFERENTIAL EXAMPLE 10

To 14 g of methyl β-amino-β-(4-methylphenyl)propionate hydrochloride, were added 200 ml of ethyl acetate and 10.2 ml of triethylamine. The mixture was stirred at room temperature for 30 minutes, then washed with saturated aqueous sodium chloride solution, dried over anhydrous magnesium sulfate, and filtered. The filtrate was evaporated under reduced pressure. To the residue, was added 8.5 g of phthalic anhydride. The mixture was stirred at 150° to 155° C. for one hour and recrystallized from an ether-n-hexane mixture to yield 15 g of methyl β-phthalimido-β-(4-methylphenyl)propionate; m.p. 97°–99° C.

REFERENTIAL EXAMPLE 11

To 50.3 g of 4-phthalimidomethyltoluene, were added 39 g of N-bromosuccinimide (NBS), 1.5 g of benzoyl peroxide (BPO), and 500 ml of carbon tetrachloride. The mixture was heated under reflux for one hour. The reaction mixture was cooled in ice, filtered from insolubles, and concentrated under reduced pressure. The residue was recrystallized from methanol to yield 40 g of colorless needle crystals of 4-phthalimidomethylbenzyl bromide; m.p. 129°–131° C.

In a similar manner, the following compounds were obtained:
3-Phthalimidomethylbenzyl bromide, m.p. 124°–126° C.
4-(1-Phthalimidoethyl)benzyl bromide, IR $\nu_{max}^{liq.film}$ cm$^{-1}$: 1770, 1700, 1605.
4-[(2-Methoxycarbonyl-1-phthalimido)ethyl]benzyl bromide, IR $\nu_{max}^{liq.film}$ cm$^{-1}$: 1770, 1730, 1700.
2-Methoxy-4-phthalimidomethylbenzyl bromide, m.p. 170.5°–171.5° C.
2-Chloro-4-phthalimidomethylbenzyl bromide, m.p. 184°–185° C.
2-Nitro-4-phthalimidomethylbenzyl bromide, m.p. 174°–178° C.

REFERENTIAL EXAMPLE 12

To 29.2 g of 4-phthalimidomethylbenzyl bromide, were added 400 ml of benzene and 23.2 g of triphenylphosphine. The mixture was heated under reflux for 2 hours. The reaction mixture was cooled in ice. The crystals precipitated out of the reaction mixture were collected by filtration and washed thoroughly with benzene to yield 35.5 g of 4-phthalimidomethylbenzyl-triphenylphosphonium bromide; m.p. 245°–246° C.

In a similar manner, the following compounds were obtained:
3-Phthalimidomethylbenzyltriphenylphosphonium bromide; m.p. 208°–210° C.
4-(1-Phthalimidoethyl)benzyltriphenylphosphonium bromide; m.p. 150°–153° C.
4-[(2-Methoxycarbonyl-1-phthalimido)ethyl]benzyltriphenylphosphonium bromide; m.p. 190°–193° C.
4-(3-Phthalimidopropyl)benzyltriphenylphosphonium chloride, m.p. 148°–153° C.
2-Chloro-4-phthalimidomethylbenzyltriphenylphosphonium bromide; m.p. 188°–190° C.
2-Methoxy-4-phthalimidomethylbenzyltriphenylphosphonium bromide; m.p. 226°–227.5° C.
4-Methylbenzyltriphenylphosphonium bromide; m.p. 266°–268.5° C.

REFERENTIAL EXAMPLE 13

A mixture comprising 10 g of 3-methyl-panisaldehyde, 5.4 g of hydroxylamine hydrochloride, 8.4 g of sodium formate, and 40 ml of formic acid was stirred at 100° C. for 3 hours. The reaction mixture was added to 400 ml of water and extracted with 300 ml of ethyl acetate. The extract was washed twice with water, then with saturated aqueous sodium hydrogencarbonate solution, dried over anhydrous magnesium sulfate, and filtered. The filtrate was concentrated under reduced pressure and the residue was recrystallized from an ether-n-hexane mixture to yield 10 g of 4-methoxy-3-methylbenzonitrile; m.p. 46°–47° C.

REFERENTIAL EXAMPLE 14

To 9.8 g of 4-methoxy-3-methylbenzonitrile, were added 150 ml of carbon tetrachloride, 10 g of NBS, and 0.4 g of BPO. The mixture was heated under reflux for 2.5 hours. The reaction mixture was cooled in ice, filtered from insolubles and concentrated under reduced pressure. The residue was admixed with n-hexane, stirred for 30 minutes, and collected by filtration to yield 9 g of 3-bromomethyl-4-methoxybenzonitrile; m.p. 102°–103° C.

REFERENTIAL EXAMPLE 15

To 5 g of 3-bromomethyl-4-methoxybenzonitrile, were added 6.2 g of hexamethylenetetramine, 10 ml of acetic acid, and 10 ml of water. The mixture was heated under reflux for 2 hours. After addition of 10 ml of concentrated hydrochloric acid, the mixture was further refluxed for 15 minutes. The reaction mixture was cooled in ice and extracted with 200 ml of ethyl acetate. The ethyl acetate layer was washed twice with 200 ml of water, then with saturated aqueous sodium hydrogencarbonate solution, dried over anhydrous magnesium sulfate, and filtered. The filtrate was concentrated under reduced pressure. Ether was added to the residue and the precipitated crystals were collected by filtration to yield 1.6 g of 3-cyano6-methoxybenzaldehyde; m.p. 119°–120° C.

REFERENTIAL EXAMPLE 16

To a solution of 6.7 g of 3-benzoyl-4-hydroxybenzamidine methanesulfonate in 150 ml of dimethylformamide, were added 8.4 ml of triethylamine and 14.1 g of S-(4-methoxybenzyloxycarbonyl)-4,6-dimethyl-2-mercaptopyrimidine. The mixture was heated overnight with stirring at 80° to 90° C. The reaction mixture was stripped of the solvent by distillation. The residue was admixed with water and extracted with ethyl acetate. The organic layer was washed with saturated aqueous sodium chloride solution, dried over anhydrous magnesium sulfate, and stripped of the solvent by distillation. The residue was subjected to silica gel column chromatography to separate and purify the intended fractions which were then recrystallized from an ethanol-n-hexane mixture to yield 5.3 g of pale yellow needle crystals of 3-benzoyl-4-hydroxy-N-(4-methoxybenzyloxycarbonyl)benzamidine; m.p. 102°-104° C.

In a similar manner the following compounds were obtained:

4-Hydroxy-3-methoxy-N-(4-methoxybenzyloxycarbonyl)benzamidine; yellow amorphous powder. PMR (CDCl$_3$) δ: 3.76(6H, S), 5.11(2H, S).

3-Hydroxy-4-methoxy-N-(4-methoxybenzyloxycarbonyl)benzamidine; m.p. 113°-115° C.

4-Hydroxy-N-(4-methoxybenzyloxycarbonyl)benzamidine; m.p. 128.5°-130.5° C. (decomp.).

REFERENTIAL EXAMPLE 17

To 250 ml of carbon tetrachloride, were added 25.0 g of methyl 4-methylbenzoate, 32.6 g of N-bromosuccinimide, and 2.0 g of benzoyl peroxide. The mixture was heated with stirring under reflux for one hour. The reaction mixture was freed from the insolubles by filtration and stripped of the solvent by distillation. To the residue dissolved in methylene chloride, were added 9.8 g of sodium cyanide, 3.9 g of triethylbenzylammonium chloride, and 10 ml of water. The mixture was stirred at room temperature for 30 minutes and then heated overnight under reflux. The reaction mixture was washed with saturated aqueous sodium chloride solution, dried over anhydrous magnesium sulfate, and stripped of the solvent by distillation. The residue was fractionated and purified by silica gel column chromatography. The intended fractions (Rf=0.41) were collected and recrystallized from an ether-n-hexane mixture to yield 18.1 g of colorless needle crystals of methyl 4-cyanomethylbenzoate; m.p. 60°-62° C.

REFERENTIAL EXAMPLE 18

To a solution of 18.0 g of methyl 4-cyanomethylbenzoate in 100 ml of dried tetrahydrofuran, while being stirred at room temperature, was added dropwise over a period of 3 hours 360 ml of 1M solution of borane-tetrahydrofuran complex in tetrahydrofuran. The mixture was then heated under reflux for 15 hours. To the reaction mixture, was added carefully 35 ml of concentrated hydrochloric acid. The mixture was stripped of the solvent by distillation. The residue was admixed with water, washed with methylene chloride, made alkaline with 100 ml of a 30% aqueous sodium hydroxide solution, and extracted repeatedly with methylene chloride. The organic layer was dried over anhydrous potassium carbonate and stripped of the solvent by distillation to yield 12.7 g of a pale yellow oil of methyl 4-(2-aminoethyl)benzoate; PMR (CDCl$_3$) δ: 1.28(2H, S), 2.57-3.27(4H, m), 3.90(3H, S), 7.26(2H, d, J=8.0 Hz), 7.97(2H, d, J=8.0 Hz).

REFERENTIAL EXAMPLE 19

To a suspension of 8.1 g of lithium aluminum hydride in 150 ml of dried ether, while being stirred at room temperature, was added dropwise over a period of 20 minutes a solution of 12.7 g of methyl 4-(2-aminoethyl)benzoate in 100 ml of dried ether. The mixture was refluxed overnight with vigorous stirring. To the reaction mixture, was added carefully an aqueous hydrogen chloride solution to decompose the excess lithium aluminum hydride. The aqueous layer was separated, made alkaline with a 30% aqueous sodium hydroxide solution, filtered from the precipitate, and repeatedly extracted with methylene chloride. The organic layer was dried over anhydrous potassium carbonate, and stripped of the solvent by distillation, leaving behind 5.6 g of a pale yellow viscous oil of 4-(2-aminoethyl)benzyl alcohol; PMR (CDCl$_3$) δ: 1.72(3H, S), 2.53-3.10 (4H, m), 4.63(2H, S), 7.17-7.35(4H, m).

REFERENTIAL EXAMPLE 20

To a mixture comprising 30.9 g of N-allylphthalimide [Nancy J. Malek and A. E. Moormaun, J. Org. Chem., 47, 5395-5397 (1982)], 30.0 g of 4-bromobenzyl alcohol, 0.36 g of palladium acetate, and 0.98 g of tri-o-tolylphosphine, were added 44.7 ml of triethylamine and 21.0 ml of acetonitrile. After flushing the vessel with nitrogen, the mixture was heated with stirring at 100° to 110° C. for 18 hours. The crude reaction product was washed thoroughly with water, dissolved in hot dimethylformamide, and filtered from a finely divided black precipitate using Celite filter aid. Water was added to the filtrate and the precipitated solid substance was collected by filtration. The solid substance was washed successively with water and ethanol, and recrystallized from acetonitrile to yield 35.5 g of pale brown needle crystals of 4-(3-phthalimido-1-propenyl)benzyl alcohol; m.p. 148°-150° C.

REFERENTIAL EXAMPLE 21

A suspension of 22.0 g of 4-(3-phthalimido-1-propenyl)benzyl alcohol in 330 ml of ethyl acetate was catalytically reduced with 2.2 g of 10% palladium-carbon used as catalyst. The reaction mixture was filtered from the palladium-carbon and stripped of the solvent by distillation to yield 21.7 g of a colorless solid of 4-(3-phthalimidopropyl)benzyl alcohol; m.p. 94°-96° C.

REFERENTIAL EXAMPLE 22

To a suspension of 9.0 g of 4-(3-phthalimido-1-propenyl)benzyl alcohol in 100 ml of ethanol, was added 1.5 g of hydrazine hydrate. The mixture was heated with stirring under reflux for 1.5 hours and the reaction mixture was stripped of the solvent. The residue was added to 5-10% hydrochloric acid and filtered from the insolubles. The filtrate was washed with methylene chloride, made alkaline with a 50% aqueous sodium hydroxide solution, and repeatedly extracted with methylene chloride. The organic layer was dried over anhydrous potassium carbonate and stripped of the solvent by distillation to yield 3.7 g of a pale yellow solid of 4-(3-amino-1-propenyl)benzyl alcohol; m.p. 122°-123° C.

In a similar manner the following compound was obtained:

4-(3-Aminopropyl)benzyl alcohol; m.p. 78°-80° C.

REFERENTIAL EXAMPLE 23

To a solution of 3.3 g of 4-(3-amino-1-propenyl)benzyl alcohol in 100 ml of anhydrous methanol, was added 7.4 g of S-(4-methoxybenzyloxycarbonyl)-4,6-dimethyl-2-mercaptopyrimidine. The mixture was stirred at room temperature for one hour. The reaction mixture was stripped of the solvent by distillation and the residue was dissolved in chloroform. The resulting solution was washed with 5% hydrochloric acid, then with saturated aqueous sodium chloride solution, dried over anhydrous magnesium sulfate, and stripped of the solvent by distillation. The residue was recrystallized from ethanol to yield 4.9 g of colorless needle crystals of 4-[3-(4-methoxybenzyloxycarbonylamino)-1-propenyl]benzyl alcohol; m.p. 125°–126° C.

In a similar manner, the following compounds were obtained:

4-[3-(4-Methoxybenzyloxycarbonylamino)propyl]benzyl alcohol; m.p. 88°–89° C.

4-[2-(4-Methoxybenzyloxycarbonylamino)ethyl]benzyl alcohol; m.p. 93°–94° C.

REFERENTIAL EXAMPLE 24

To 60 ml of chloroform, was added 4.3 g of 4-[3-(4-methoxybenzyloxycarbonylamino)-1-propenyl]benzyl alcohol followed by 2.0 ml of triethylamine. To the mixture, while being cooled in ice and stirred, was added slowly dropwise 2.6 g of thionyl chloride. The mixture was then stirred at room temperature for 2 hours. The reaction mixture was filtered from a yellow precipitate, and stripped of the solvent by distillation. The residue was fractionated and purified by silica gel column chromatography (chloroform). The intended fractions (Rf=0.5) were collected and recrystallized from an ether-petroleum ether mixture to yield 1.7 g of colorless needle crystals of 4-[3-(4-methoxybenzyloxycarbonylamino)-1-propenyl]benzyl chloride; m.p. 111°–112° C.

In a similar manner, the following compounds were obtained:

4-[3-(4-Methoxybenzyloxycarbonylamino)propyl]benzyl chloride (Rf=0.64, chloroform:methanol=50:1); m.p. 82°–84° C.

4-(3-Phthalimidopropyl)benzyl chloride; m.p. 82°–84° C.

4-[2-(4-Methoxybenzyloxycarbonylamino)ethyl]benzyl chloride (Rf=0.35, chloroform); m.p. 93°–94° C.

EXAMPLE 1

Into 800 ml of anhydrous methanol, was dissolved 35.5 g of 4-phthalimidomethylbenzyltriphenylphosphonium bromide. To the resulting solution, through which argon had been passed with stirring for 5 minutes, was added at room temperature slowly dropwise 11.6 ml of anhydrous methanol containing 28% of sodium methoxide. After 10 minutes, 7.9 g of p-cyanobenzaldehyde was added to the reaction mixture and the mixture was stirred at room temperature for 15 hours. The precipitated crystals were collected by filtration to obtain 15.4 g of 4-[2-(4-phthalimidomethylphenyl)ethenyl]benzonitrile.

IR $\nu_{max}^{KBr}$ cm$^{-1}$: 2225, 1760, 1705, 1600, 1390.

In a similar manner, the following compounds were obtained:

3-[2-(4-Phthalimidomethylphenyl)ethenyl]benzonitrile.
IR $\nu_{max}^{KBr}$ cm$^{-1}$: 2250, 1760, 1715, 1390.

4-[2-(3-Phthalimidomethylphenyl)ethenyl]benzonitrile.
IR $\nu_{max}^{KBr}$ cm$^{-1}$: 2225, 1760, 1700, 1390.

3-[2-(3-Phthalimidomethylphenyl)ethenyl]benzonitrile.
IR $\nu_{max}^{KBr}$ cm$^{-1}$: 2225, 1760, 1695, 1420, 1385.

4-{2-[4-(1-Phthalimidoethyl)phenyl]ethenyl}benzonitrile.
IR $\nu_{max}^{KBr}$ cm$^{-1}$: 2225, 1770, 1705, 1595, 1385.

4-{2-[4-(2-Methoxycarbonyl-1-phthalimidoethyl)-phenyl]ethenyl}benzonitrile.
IR $\nu_{max}^{liq.film}$ cm$^{-1}$: 2225, 1770, 1730, 1700.

4-Methoxy-3-[2-(4-phthalimidomethylphenyl)ethenyl]benzonitrile.
IR $\nu_{max}^{KBr}$ cm$^{-1}$: 2225, 1760, 1705, 1390.

4-{2-[4-(3-Phthalimidopropyl)phenyl]ethenyl}benzonitrile.
IR $\nu_{max}^{KBr}$ cm$^{-1}$: 2220, 1760, 1700, 1595, 1395, 1363.

4-[2-(2-Methoxy-4-phthalimidomethylphenyl)ethenyl]benzonitrile.
IR $\nu_{max}^{KBr}$ cm$^{-1}$: 2210, 1760, 1700, 1595, 1383.

4-[2-(2-Chloro-4-phthalimidomethylphenyl)ethenyl]benzonitrile.
IR $\nu_{max}^{KBr}$ cm$^{-1}$: 2220, 1760, 1700, 1383.

4-[2-(4-Methylphenyl)ethenyl]benzonitrile; m.p. 182°–183° C. (trans), 62°–64° C. (cis).

4-[2-(4-Bromomethylphenyl)ethenyl]benzonitrile; m.p. 151°–154° C.

4-[2-(4-Dimethylaminomethylphenyl)ethenyl]benzonitrile; m.p. 82°–85° C.

EXAMPLE 2

Catalytic reduction of a solution of 9 g of 4-[2-(4-phthalimidomethylphenyl)ethenyl]benzonitrile in 300 ml of chloroform was carried out with 2 g of a 5% palladium-carbon as catalyst. The reaction mixture was filtered from the spent catalyst and the filtrate was concentrated under reduced pressure. Ether was added to the residue and the precipitated crystals were collected by filtration to obtain 8.5 g of 4-[2-(4-phthalimidomethylphenyl)ethyl]benzonitrile; m.p. 194°–197° C.

In a similar manner, the following compounds were obtained:

3-[2-(4-Phthalimidomethylphenyl)ethyl]benzonitrile; m.p. 178°–179° C.

4-[2-(3-Phthalimidomethylphenyl)ethyl]benzonitrile; m.p. 140°–141° C.

3-[2-(3-Phthalimidomethylphenyl)ethyl]benzonitrile; m.p. 119°–121° C.

4-{2-[4-(1-Phthalimidoethyl)phenyl]ethyl}benzonitrile; m.p. 145°–146° C.

4-{2-[4-(2-Methoxycarbonyl-1-phthalimidoethyl)-phenyl]ethyl}benzonitrile; IR $\nu_{max}^{liq.film}$ cm$^{-1}$: 2225, 1770, 1735, 1700.

4-Methoxy-3-[2-(4-phthalimidomethylphenyl)ethyl]benzonitrile; m.p. 150°–151° C.

4-{2-[4-(3-Phthalimidopropyl)phenyl]ethyl}benzonitrile; m.p. 110°–111° C.

4-[2-(2-Methoxy-4-phthalimidomethylphenyl)ethyl]benzonitrile; m.p. 144°–146° C.

4-[2-(2-Chloro-4-phthalimidomethylphenyl)ethyl]benzonitrile; m.p. 158°–159° C.

4-[2-(4-Dimethylaminomethylphenyl)ethyl]benzonitrile; m.p. 48°–50° C.

4-[2-(2-Nitro-4-phthalimidomethylphenyl)ethyl]benzonitrile; m.p. 164°–170° C.

EXAMPLE 3

To a solution of 6 g of 4-[2-(4-phthalimidomethylphenyl)ethyl]benzonitrile in 300 ml of chloroform, was added at room temperature slowly dropwise 50 ml of anhydrous methanol saturated with anhydrous hydrogen chloride. The mixture was stirred at room temperature for 15 hours. The reaction mixture was stripped of the solvent under reduced pressure. Ether was added to the residue and the precipitated crystals were collected by filtration to yield 6 g of methyl 4-[2-(4-phthalimidomethylphenyl)ethyl]benzimidate hydrochloride; m.p. 238°–240° C.

In a similar manner, the following compounds were obtained:

Methyl 3-[2-(4-phthalimidomethylphenyl)ethyl]benzimidate hydrochloride; m.p. 170°–172° C.

Methyl 4-[2-(3-phthalimidomethylphenyl)ethyl]benzimidate hydrochloride; m.p. 185°-187° C. (decomp.).
Methyl 3-[2-(3-phthalimidomethylphenyl)ethyl]benzimidate hydrochloride; m.p. 110°-111° C. (decomp.).
Methyl 4-{2-[4-(1-phthalimidoethyl)phenyl]ethyl}benzimidate hydrochloride; m.p. 125°-128° C.
Methyl 4-{2-[4-(2-methoxycarbonyl-1-phthalimidoethyl)phenyl]ethyl}benzimidate hydrochloride;
IR $\nu_{max}^{KBr}$ cm$^{-1}$: 3000, 1770, 1730, 1700, 1650, 1600.
Methyl 4-methoxy-3-[2-(4-phthalimidomethylphenyl)ethyl]benzimidate hydrochloride; m.p. 141°-142° C.
Methyl 4-{2-[4-(3-phthalimidopropyl)phenyl]ethyl}benzimidate hydrochloride; m.p. 190°-191° C.
Methyl 4-[2-(2-methoxy-4-phthalimidomethylphenyl)ethyl]benzimidate hydrochloride; m.p. 203°-206° C.
Methyl 4-[2-(2-chloro-4-phthalimidomethylphenyl)ethyl]benzimidate hydrochloride; m.p. 210°-212° C.
Methyl 4-[2-(2-nitro-4-phthalimidomethylphenyl)ethyl]benzimidate hydrochloride; m.p. 214°-218° C.

EXAMPLE 4

To a solution of 1.7 g of 4-[2-(4-phthalimidomethylphenyl)ethenyl]benzonitrile in 100 ml of chloroform was added at room temperature slowly dropwise 30 ml of anhydrous methanol saturated with anhydrous hydrogen chloride. The mixture was stirred at room temperature for 15 hours. The reaction mixture was stripped of the solvent under reduced pressure. Ether was added to the residue and the precipitated crystals were collected by filtration to yield 1.6 g of methyl 4-[2-(4-phthalimidomethylphenyl)ethenyl]benzimidate hydrochloride; m.p. 230°-234° C. (decomp.).

EXAMPLE 5

To a solution of 1.8 g of methyl 4-{2-[4-(1-phthalimidoethyl)phenyl]ethyl}benzimidate hydrochloride in 30 ml of anhydrous methanol, was added 2.3 ml of a solution of anhydrous ammonia in anhydrous methanol (0.036 g/ml). The mixture was stirred at room temperature for 15 hours. The reaction mixture was stripped of the solvent under reduced pressure. Ether was added to the residue and the precipitated crystals were collected by filtration to yield 1.6 g of 4-{2-[4-(1-phthalimidoethyl)phenyl]ethyl}benzamidine hydrochloride; m.p. 110°-115° C.

In a similar manner, the following compounds were obtained:
4-[2-(4-Phthalimidomethylphenyl)ethyl]benzamidine hydrochloride; m.p. 230°-231° C.
4-{2-[4-(2-Methoxycarbonyl-1-phthalimidoethyl)phenyl]ethyl}benzamidine hydrochloride; m.p. 100°-105° C. (decomp.).
4-{2-[4-(3-Phthalimidopropyl)phenyl]ethyl}benzamidine hydrochloride; m.p. 186°-188° C.

EXAMPLE 6

To a solution of 1.5 g of methyl 4-[2-(4-phthalimidomethylphenyl)ethyl]benzimidate hydrochloride in 150 ml of chloroform, was added 0.3 ml of a methanol solution containing 40% of methylamine. The mixture was stirred at room temperature for 15 hours. The reaction mixture was stripped of the solvent under reduced pressure. Ether was added to the residue and the precipitated crystals were collected by filtration to yield 1.3 g of N-methyl-4-[2-(4-phthalimidomethylphenyl)ethyl]benzamidine hydrochloride; m.p. 270° C. or above.

In a similar manner, the following compounds were obtained:
N-n-Butyl-4-[2-(4-phthalimidomethylphenyl)ethyl]benzamidine hydrochloride; m.p. 270° C.
N-(3-Morpholinopropyl)-4-[2-(4-phthalimidomethylphenyl)ethyl]benzamidine hydrochloride; m.p. 178°-180° C.
N-(2-Phenylethyl)-4-[2-(4-phthalimidomethylphenyl)ethyl]benzamidine hydrochloride; m.p. 263°-265° C.
N-Methyl-3-[2-(4-phthalimidomethylphenyl)ethyl]benzamidine hydrochloride; m.p. 182°-184° C.
N-Methyl-4-[2-(3-phthalimidomethylphenyl)ethyl]benzamidine hydrochloride; m.p. 170°-175° C.
N-Methyl-3-[2-(3-phthalimidomethylphenyl)ethyl]benzamidine hydrochloride; m.p. 100°-105° C. (decomp.).
4-[2-(4-Phthalimidomethylphenyl)ethyl]-N-[2-(2-pyridyl)ethyl]benzamidine hydrochloride; m.p. 195°-198° C. (decomp.).
4-Methoxy-N-methyl-3-[2-(4-phthalimidomethylphenyl)ethyl]benzamidine hydrochloride; m.p. 104°-107° C.
4-[2-(2-Methoxy-4-phthalimidomethylphenyl)ethyl]-N-methylbenzamidine; m.p. 136°-139° C.
4-[2-(2-Chloro-4-phthalimidomethylphenyl)ethyl]-N-methylbenzamidine; m.p. 210°-213° C.
N-(2-Methoxyethyl)-4-[2-(4-phthalimidomethylphenyl)ethyl]benzamidine hydrochloride; m.p. 170°-173° C. (decomp.).
N-Cyclohexyl-4-[2-(4-phthalimidomethylphenyl)ethyl]benzamidine hydrochloride; m.p. 203°-208° C. (decomp.).
N-[2-(4-Nitrophenyl)ethyl]-4-[2-(4-phthalimidomethylphenyl)ethyl]benzamidine hydrochloride; m.p. 215°-216° C.
N-[2-(4-Methoxyphenyl)ethyl]-4-[2-(4-phthalimidomethylphenyl)ethyl]benzamidine hydrochloride; m.p. 235°-238° C.
N-(3-Pyridylmethyl)-4-[2-(4-phthalimidomethylphenyl)ethyl]benzamidine hydrochloride; m.p. 155°-157° C.
N-[2-(3,4-Dimethoxyphenyl)ethyl]-4-[2-(4-phthalimidomethylphenyl)ethyl]benzamidine hydrochloride; m.p. 195°-197° C.
N-Methoxy-4-[2-(4-phthalimidomethylphenyl)ethyl]benzamidine hydrochloride; m.p. 217°-222° C.

EXAMPLE 7

To 1 g of methyl 4-[2-(4-phthalimidomethylphenyl)ethenyl]benzimidate hydrochloride, were added 60 ml of chloroform and 0.2 ml of a methanol solution containing 40% of methylamine. The mixture was stirred at room temperature for 15 hours and stripped of the solvent under reduced pressure. Ether was added to the residue and the precipitated crystals were collected by filtration to yield 0.33 g of N-methyl-4-[2-(4-phthalimidomethylphenyl)ethenyl]benzamidine hydrochloride; m.p. ≧280° C.

EXAMPLE 8

To a solution of 2 g of methyl 4-[2-(4-phthalimidomethylphenyl)ethenyl]benzimidate hydrochloride in 200 ml of chloroform, was added 3.4 ml of a solution of anhydrous ammonia in anhydrous methanol (0.028 g/ml). The mixture was stirred at room temperature for 15 hours and stripped of the solvent under reduced pressure. The residue was recrystallized from a dimethylformamidemethanol mixture to yield 1 g of colorless granular crystals of 4-[2-(4-phthalimidomethylphenyl)ethenyl]benzamidine hydrochloride; IR $\nu_{max}^{KBr}$ cm$^{-1}$: 1770, 1700, 1625, 1600.

EXAMPLE 9

To 800 mg of N-methyl-4-[2-(4-phthalimidomethylphenyl)ethyl]benzamidine hydrochloride, were added 20 ml of methanol and 25 ml of concentrated hydrochloric acid. The mixture was heated under reflux for 18 hours. After cooling, the reaction mixture was filtered from the insolubles and concentrated under reduced pressure. The residue was recrystallized from a methanol-acetone mixture to yield 310 mg of colorless granular crystals of 4-[2-(4-aminomethylphenyl)ethyl]-N-methylbenzamidine dihydrochloride; m.p. ≧280° C.

In a similar manner, the following compounds were obtained:

4-{2-[4-(1-Aminoethyl)phenyl]ethyl}benzamidine dihydrochloride; m.p. 165°–168° C. (decomp.).

4-[2-(4-Aminomethylphenyl)ethyl]benzamidine dihydrochloride; m.p. ≧260° C.

4-{2-[4-(1-Amino-2-methoxycarbonylethyl)phenyl]ethyl}benzamidine dihydrochloride; m.p. 105°–110° C. (decomp.).

4-{2-[4-(3-Aminopropyl)phenyl]ethyl}benzamidine dihydrochloride; m.p. 272°–275° C. (decomp.).

4-[2-(4-Aminomethyl-2-methoxyphenyl)ethyl]-N-methylbenzamidine dihydrochloride; m.p. 238°–242° C. (decomp.).

4-[2-(4-Aminomethyl-2-chlorophenyl)ethyl]-N-methylbenzamidine dihydrochloride; m.p. 273°–275° C. (decomp.).

4-[2-(4-Aminomethylphenyl)ethyl]-N-n-butyl-benzamidine dihydrochloride; m.p. 220°–222° C.

4-[2-(4-Aminomethylphenyl)ethyl]-N-(3-morpholinopropyl)benzamidine trihydrochloride; m.p. 110°–115° C. (decomp.).

4-[2-(4-Aminomethylphenyl)ethyl]-N-(2-phenylethyl)benzamidine dihydrochloride; m.p. 265°–266° C.

3-[2-(4-Aminomethylphenyl)ethyl]-N-methylbenzamidine dihydrochloride; m.p. 211°–213° C.

4-[2-(3-Aminomethylphenyl)ethyl]-N-methylbenzamidine dihydrochloride; m.p. 230°–235° C. (decomp.).

3-[2-(3-Aminomethylphenyl)ethyl]-N-methylbenzamidine dihydrochloride; m.p. 125°–130° C. (decomp.).

4-[2-(4-Aminomethylphenyl)ethyl]-N-[2-(2-pyridyl)ethyl]benzamidine trihydrochloride; m.p. 247°–248° C.

3-[2-(4-Aminomethylphenyl)ethyl]-4-methoxy-N-methylbenzamidine dihydrochloride; m.p. 164°–166° C.

4-[2-(4-Aminomethylphenyl)ethyl]-N-(2-methoxyethyl)benzamidine dihydrochloride; m.p. 204°–207° C.

4-[2-(4-Aminomethylphenyl)ethyl]-N-cyclohexylbenzamidine dihydrochloride; m.p. 215°–217° C.

4-[2-(4-Aminomethylphenyl)ethyl]-N-[2-(4-nitrophenyl)ethyl]benzamidine dihydrochloride; m.p. 265°–267° C. (decomp.).

4-[2-(4-Aminomethylphenyl)ethyl]-N-[2-(4-aminophenyl)ethyl]benzamidine trihydrochloride; m.p. 275°–278° C. (decomp.).

4-[2-(4-Aminomethylphenyl)ethyl]-N-[2-(4-methoxyphenyl)ethyl]benzamidine dihydrochloride; m.p. 265°–270° C. (decomp.).

4-[2-(4-Aminomethylphenyl)ethyl]-N-(3-pyridylmethyl)benzamidine trihydrochloride; m.p. 263°–265° C. (decomp.).

4-[2-(4-Aminomethylphenyl)ethyl]-N-[2-(3,4-dimethoxyphenyl)ethyl]benzamidine dihydrochloride; m.p. 165°–168° C.

4-[2-(4-Aminomethylphenyl)ethyl]-N-[2-(3,4-dihydroxyphenyl)ethyl]benzamidine dihydrochloride; m.p. 205°–210° C.

4-[2-(4-Aminomethylphenyl)ethyl]-N-[2-(4-hydroxyphenyl)ethyl]benzamidine dihydrochloride; m.p. 248°–251° C.

N-Methyl-4-[2-(4-aminomethyl-2-nitrophenyl)ethyl]benzamidine dihydrochloride; m.p. ca. 244° C. (decomp.).

N-Methyl-4-[2-(2-amino-4-aminomethylphenyl)ethyl]benzamidine trihydrochloride; m.p. ca. 262° C. (decomp.).

N,N-Dimethyl-4-[2-(4-aminomethylphenyl)ethyl]benzamidine dihydrochloride; m.p. 290° C.< (decomp.).

N,N'-Dimethyl-4-[2-(4-aminomethylphenyl)ethyl]benzamidine dihydrobromide; m.p. 265°–266° C.

N-Methoxy-4-[2-(4-aminomethylphenyl)ethyl]benzamidine dihydrochloride; m.p. 235°–237° C.

2-{4-[2-(4-Aminomethylphenyl)ethyl]phenyl}imidazoline dihydrochloride; m.p. >300° C.

2-{4-[2-(4-Aminomethylphenyl)ethyl]phenyl}-1-methylimidazoline dihydrochloride; m.p. 271°–274° C. (decomp.).

2-{4-[2-(4-Aminomethylphenyl)ethyl]phenyl}-5-methylimidazoline dihydrochloride; m.p. 269°–273° C. (decomp.).

N-(2-Aminoethyl)-3-[2-(4-aminomethylphenyl)ethyl]-4-methoxybenzamidine trihydrochloride; m.p. 249°–254° C. (decomp.).

2-{3-[2-(4-Aminomethylphenyl)ethyl]-4-methoxyphenyl}imidazoline dihydrochloride; m.p. 253°–256° C. (decomp.).

3-Amino-4-[2-(4-aminomethylphenyl)ethyl]-N-methylbenzamidine trihydrochloride; m.p. 276°–279° C. (decomp.).

4-[2-(4-Aminomethylphenyl)ethyl]-N-methyl-3-nitrobenzamidine dihydrochloride; m.p. 118°–122° C. (decomp.).

N-Methyl-4-[2-(4-dimethylaminomethylphenyl)ethyl]benzamidine dihydrochloride; m.p. 198°–200° C.

4-[2-(4-Aminomethyl-2-methoxyphenyl)ethyl]-N,N'-dimethylbenzamidine dihydrochloride; m.p. 258° C. (decomp.).

4-[2-(4-Methylaminomethylphenyl)ethyl]-N-methylbenzamidine dihydrochloride; m.p. 155°–160° C.

4-[2-(4-Aminomethyl-2-nitrophenyl)ethyl]-N,N'-dimethylbenzamidine dihydrochloride; m.p. 256°–258° C. (decomp.).

4-[2-(4-Aminomethylphenyl)ethyl]-N-(4-aminomethylphenyl)methylbenzamidine trihydrochloride; m.p. 299° C. (decomp.).

4-[2-(4-Aminomethyl-2-methoxyphenyl)ethyl]-N-[2-(2-pyridyl)ethyl]benzamidine trihydrochloride; m.p. 214° C. (decomp.).

4-[2-(4-Aminomethyl-2-methoxyphenyl)ethyl]-N-(2-pyridylmethyl)benzamidine trihydrochloride; m.p. 242° C. (decomp.).

2-{4-[2-(4-Aminomethyl-2-methoxyphenyl)ethyl]phenyl}imidazoline dihydrochloride; m.p. 287° C. (decomp.).

EXAMPLE 10

To 150 mg of N-methyl-4-[2-(4-phthalimidomethylphenyl)ethenyl]benzamidine hydrochloride, were added 30 ml of methanol and 30 ml of concentrated hydrochloric acid. The mixture was heated under reflux for 2 days. After cooling, the reaction mixture was filtered from the insolubles and concentrated under reduced pressure. The residue was recrystallized from a methanol-acetone mixture to yield 105 mg of colorless granular crystals of 4-[2-(4-aminomethylphenyl)ethenyl]-N-methylbenzamidine dihydrochloride. IR $\nu_{max}^{KBr}$ cm$^{-1}$: 3075, 2925, 2850, 1670, 1615, 1600.

EXAMPLE 11

A solution of 30 mg of 4-[2-(4-aminomethylphenyl)ethenyl]benzamidine dihydrochloride in 30 ml of methanol was catalytically reduced with 20 mg of a 5% palladium-carbon as catalyst. The reaction mixture was filtered from spent catalyst and concentrated under reduced pressure. The residue was recrystallized from a methanolisopropanol-ether mixture to yield 20 mg of 4-[2-(4-aminomethylphenyl)ethyl]benzamidine dihydrochloride; m.p. ≧260° C.

EXAMPLE 12

To 240 ml of dried acetone, were added 23.8 g of p-xylene dibromide, 7.1 g of 4-cyanophenol, 8.3 g of anhydrous potassium carbonate, and 0.7 g of potassium iodide. The mixture was heated with stirring under reflux for 2 hours. The hot reaction mixture was filtered from the insolubles and stripped of the solvent by distillation. The residue was recrystallized from chloroform to remove the excess p-xylene dibromide. The filtrate was fractionated and purified by silica gel column chromatography (chloroform) to yield 9.1 g of colorless solid 4-(4-bromomethylbenzyloxy)benzonitrile; Rf=0.58, m.p. 122°-123° C.

EXAMPLE 13

To a solution of 3.0 g of 4-(4-bromomethylbenzyloxy)benzonitrile in 30 ml of N,N-dimethylformamide, was added at room temperature 2.7 ml of a 50% aqueous dimethylamine solution. The mixture was stirred for 30 minutes. The reaction mixture was diluted with water and extracted with ether. The ether layer was washed with saturated aqueous sodium chloride solution, dried over anhydrous magnesium sulfate, and stripped of the solvent to yield 2.4 g of colorless solid 4-(4-dimethylaminomethylbenzyloxy)benzonitrile; m.p. 78°-79° C.

EXAMPLE 14

To 30 ml of anhydrous methanol, which had been saturated with anhydrous hydrogen chloride while cooling in ice, was added 2.0 g of 4-(4-dimethylaminomethylbenzyloxy)benzonitrile. The mixture was stirred overnight at room temperature and stripped of the solvent by distillation at low temperatures. The residue was washed with dried ether to yield 2.6 g of pale yellow solid methyl 4-(4-dimethylaminomethylbenzyloxy)benzimidate dihydrochloride. IR $\nu_{max}^{KBr}$ cm$^{-1}$: 3370, 2900, 2680, 1602, 1260.

EXAMPLE 15

A solution of 2.4 g of methyl 4-(4-dimethylaminomethylbenzyloxy)benzimidate dihydrochloride in 35 ml of anhydrous methanol was saturated with anhydrous ammonia while cooling in ice. The mixture was then stirred at room temperature for 2 days. The reaction mixture was concentrated to a point, beyond which crystals would be precipitated, and the concentrated mixture was cooled in ice to obtain 1.5 g of a colorless solid. To the solid were added a small amount of methanol and an excess of methanesulfonic acid. Acetone was added to the resulting solution to precipitate a colorless solid which was recrystallized three times from ethanol to yield 0.7 g of colorless needle crystals of 4-(4-dimethylaminomethylbenzyloxy)benzamidine methanesulfonate; m.p. 125°-126° C. (decomp.).

EXAMPLE 16

To 50 ml of dried acetone, were added 5.0 g of 4-phthalimidomethylbenzyl bromide, 2.5 g of 4-cyano-2-methoxyphenol, 2.3 g of anhydrous potassium carbonate, and 0.25 g of potassium iodide. The mixture was heated with stirring under reflux for one hour and then stripped of the solvent by distillation. The residue was washed thoroughly with water and recrystallized from a methanolethyl acetate mixture to yield 5.3 g of colorless prismatic crystals of 3-methoxy-4-(4-phthalimidomethylbenzyloxy)benzonitrile; m.p. 171°-172° C.

In a similar manner the following compounds were obtained:

4-(4-Aminomethyl-2-methoxyphenoxymethyl)-N-methylbenzamidine dihydrochloride; m.p. 273°-275° C. (decomp.).

4-(4-Aminomethylphenoxymethyl)-N-methylbenzamidine dihydrochloride; m.p. 266°-269° C.

EXAMPLE 17

To a mixture of 25 ml of chloroform and 50 ml of anhydrous methanol saturated with anhydrous hydrogen chloride while cooling in ice, was added 4.8 g of 3-methoxy-4-(4-phthalimidomethylbenzyloxy)benzonitrile. The mixture was stirred at room temperature for 24 hours, then concentrated, and admixed with ethyl acetate to yield 3.4 g of colorless or pink solid methyl 3-methoxy-4-(4-phthalimidomethylbenzyloxy)benzimidate hydrochloride; m.p. 221°-222° C.

EXAMPLE 18

To a mixture of 100 ml of chloroform and 100 ml of anhydrous methanol, was added 3.0 g of methyl 3-methoxy-4-(4-phthalimidomethylbenzyloxy)benzimidate hydrochloride followed by 16 ml of a methanol solution of anhydrous ammonia (22 mg/ml). The mixture was stirred for 24 hours and then evaporated to dryness. The residue was dissolved in methanol, then poured into a large volume of chloroform, and filtered from precipitated colorless solids. The filtrate was evaporated to dryness and the residue was recrystallized from methanol to yield 1.4 g of 3-methoxy-4-(4-phthalimidomethylbenzyloxy)benzamidine; m.p. 228°-230° C. To obtain a methanesulfonate, the above benzamidine compound was suspended in methanol and admixed with an excess of methanesulfonic acid. Upon addition of ether to the resulting solution, there was obtained a colorless solid which was recrystallized from methanol to yield colorless needle crystals of 3-methoxy-4-(4-phthalimidomethylbenzyloxy)benzamidine methanesulfonate; m.p. 174°-176° C.

EXAMPLE 19

To 15 ml of methanol was added 416 mg of 3-methoxy-4-(4-phthalimidomethylbenzyloxy)benzamidine followed by 3.1 ml of a 40% methylamine-methanol solution. The mixture was heated under reflux for 4 hours and stripped of the solvent and excess methylamine by distillation. To the residue was added 3 ml of a 16% hydrogen chloride gas-methanol solution. After the solvent was distilled off, the residue was recrystallized from methanolacetonitrile to yield 193 mg of colorless solid 4-(4-aminomethylbenzyloxy)-3-methoxy-N-methylbenzamidine dihydrochloride; m.p. 218°-220° C. (decomp.).

EXAMPLE 20

To 200 ml of dried acetone, were added 12.0 g of p-xylene dibromide, 4.5 g of 3-benzoyl-4-hydroxy-N-(4-methoxybenzyloxycarbonyl)benzamidine, 1.7 g of anhydrous potassium carbonate, and 0.7 g of potassium iodide. The mixture was heated with stirring under reflux for 3 hours. The hot reaction mixture was filtered from the insolubles and stripped of the solvent by distillation. A suitable amount of chloroform was added to the residue and filtered from the excess p-xylene dibromide. The filtrate was fractionated and purified by silica gel column chromatography (chloroform:ethyl acetate=10:1). The intended fractions (Rf=0.24) were collected to obtain 4.2 g of an amorphous powder of 4-(4-bromomethylbenzyloxy)-3-benzoyl-N-(4-methoxybenzyloxycarbonyl)benzamidine.

PMR (CDCl$_3$) δ: 3.75(3H, S), 4.39(2H, S), 4.95 (2H, S), 5.09(2H, S), 6.50-8.31(18H, m).

In a similar manner the following compounds were obtained:

4-(4-Bromomethylbenzyloxy)-N-(4-methoxybenzyloxycarbonyl)benzamidine; Rf=0.36, chloroform:ethyl acetate=6:1; m.p. 115°-118° C. (decomp.).

4-(3-Bromomethylbenzyloxy)-N-(4-methoxybenzyloxycarbonyl)benzamidine; Rf=0.64, chloroform:methanol=10:0.3; m.p. 114°-116° C. (decomp.).

4-(4-Bromomethylbenzyloxy)-3-methoxy-N-(4-methoxybenzyloxycarbonyl)benzamidine; Rf=0.51, chloroform:methanol=50:1; m.p. 111°-112° C. (decomp.).

3-(4-Bromomethylbenzyloxy)-4-methoxy-N-(4-methoxybenzyloxycarbonyl)benzamidine; Rf=0.34, chloroform:ethyl acetate=10:1; yellow viscous oil.

IR $\Gamma_{max}^{KBr}$ cm$^{-1}$: 3390, 3260, 2940, 1660, 1595, 1565.

EXAMPLE 21

To a mixture of 30 ml of N,N-dimethylformamide and 19 ml of aqueous ammonia (25-28%), while being stirred at room temperature, was added dropwise 20 ml of an N,N-dimethylformamide solution containing 1.5 g of 4-(4-bromomethylbenzyloxy)-N-(4-methoxybenzyloxycarbonyl)benzamidine. The mixture was stirred for 30 minutes, then filtered from the precipitate (a secondary amine), and stripped of the solvent by distillation. The residue was washed with water, then with ethanol, and recrystallized from N,N-dimethylformamide to yield 0.96 g of colorless solid 4-(4-aminomethylbenzyloxy)-N-(4-methoxybenzyloxycarbonyl)benzamidine; m.p. 160°-161° C. (decomp.).

In a similar manner the following compounds were obtained:

4-(3-Aminomethylbenzyloxy)-N-(4-methoxybenzyloxycarbonyl)benzamidine; m.p. 116°-118° C. (decomp.).

4-(4-Aminomethylbenzyloxy)-3-methoxy-N-(4-methoxybenzyloxycarbonyl)benzamidine; pale yellow amorphous powder; IR $\nu_{max}^{KBr}$ cm$^{-1}$: 3370, 3160, 2990, 2920, 1650, 1600, 1580, 1485.

3-(4-Aminomethylbenzyloxy)-4-methoxy-N-(4-methoxybenzyloxycarbonyl)benzamidine; colorless viscous oil;

IR $\nu_{max}^{neat}$ cm$^{-1}$: 3360, 3310, 2950, 1700, 1610, 1580, 1490, 1435, 1245, 1118, 1020.

4-(4-Aminomethylbenzyloxy)-3-benzoyl-N-(4-methoxybenzyloxycarbonyl)benzamidine; colorless amorphous powder; IR $\nu_{max}^{KBr}$ cm$^{-1}$: 2950, 1650, 1600, 1555, 1475, 1395, 1255.

By the reaction with other amines, the following compounds were obtained:

4-(4-Methylaminomethylbenzyloxy)-N-(4-methoxybenzyloxycarbonyl)benzamidine; m.p. 127°-129° C. (decomp.).

4-[4-(4-Methyl-1-piperazinylmethyl)benzyloxy]-N-(4-methoxybenzyloxycarbonyl)benzamidine; m.p. 143°-145° C. (decomp.).

4-[4-(4-Morpholinomethyl)benzyloxy]-N-(4-methoxybenzyloxycarbonyl)benzamidine; m.p. 139°-141° C. (decomp.).

4-[4-(1-Imidazolinylmethyl)benzyloxy]-3-methoxy-N-(4-methoxybenzyloxycarbonyl)benzamidine; colorless amorphous powder; IR $\nu_{max}^{KBr}$ cm$^{-1}$: 3300, 3100, 1610, 1500, 1220, 1205.

4-(4-Aminomethylbenzyloxy)-N-(3,4,5-trimethoxybenzoyl)benzamidine dimethanesulfonate; m.p. 192°-196° C.

EXAMPLE 22

To 40 ml of acetic acid, was added 1.63 g of 4-(4-aminomethylbenzyloxy)-N-(4-methoxybenzyloxycarbonyl)benzamidine. The mixture was heated under reflux for 10 minutes. The precipitate was collected by filtration and washed with ether to yield 0.66 g of colorless solid 4-(4-aminomethylbenzyloxy)benzamidine; m.p. >280° C. Ether was added to the filtrate to yield 0.43 g of 4-(4-aminomethylbenzyloxy)benzamidine diacetate; m.p. 177°-178° C. (decomp.)

In a similar manner the following compounds were obtained:

4-(4-Methylaminomethylbenzyloxy)benzamidine diacetate; m.p. 186°-187° C. (decomp.).

4-[4-(4-Methyl-1-piperazinylmethyl)benzyloxy]benzamidine acetate; m.p. 201°-202° C. (decomp.).

4-[4-(4-Morpholinomethyl)benzyloxy]benzamidine acetate; m.p. 199°-201° C. (decomp.).

4-(3-Aminomethylbenzyloxy)benzamidine acetate m.p. 174°-176° C. (decomp.).

4-(4-Aminomethylbenzyloxy)-3-methoxybenzamidine; m.p. 201°-202° C. (decomp.).

4-[4-(1-Imidazolylmethyl)benzyloxy]-3-methoxybenzamidine dimethanesulfonate; colorless oil;

IR $\nu_{max}^{KBr}$ cm$^{-1}$: 3350, 3100, 1660, 1595, 1485.

3-(4-Aminomethylbenzyloxy)-4-methoxybenzamidine diacetate; m.p. 188°-190° C. (decomp.).

4-(4-Aminomethylbenzyloxy)-3-benzoylbenzamidine acetate; m.p. 158°-160° C. (decomp.).

EXAMPLE 23

To a solution of 100 mg of 4-(3-aminomethylbenzyloxy)-N-(4-methoxybenzyloxycarbonyl)benzamidine in 5 ml of methanol, was added 1 ml of a methanol solution containing 40% of methylamine. The mixture was heated under reflux for 30 minutes and then stripped of the solvent and excess methylamine by distillation. To the residue was added 2 ml of a 10% methanol solution of anhydrous hydrogen chloride. Ether was added to the resulting solution to separate a viscous oil which was treated with an ethanolether mixture to yield 60 mg of pale yellow solid 4-(3-aminomethylbenzyloxy)-N-methylbenzamidine dihydrochloride; IR $\nu_{max}^{KBr}$ cm$^{-1}$: 3400, 3110, 1662, 1617, 1602, 1500, 1258.

EXAMPLE 24

To a suspension of 300 mg of 4-(3-bromomethyl-benzyloxy)-N-(4-methoxybenzyloxycarbonyl)benzamidine in 5 ml of methanol, was added 2.4 ml of a methanol solution containing 40% of methylamine. The mixture was heated with stirring under reflux for 2.5 hours and then stripped of the solvent and excess methylamine by distillation. To the residue was added 5 ml of a methanol solution containing 10% of anhydrous hydrogen chloride. The solvent was removed by distillation and the residue was recrystallized from an ethanol-acetonitrile mixture to yield 98 mg of colorless solid 4-(3-methylaminomethylbenzyloxy)-N-methylbenzamidine dihydrochloride, m.p. 222°–224° C. (decomp.).

EXAMPLE 25

To 50 ml of dried acetone, were added 2.0 g of 4-phthalimidomethylbenzyl bromide, 2.4 g of 3-benzoyl-4-hydroxy-N-(4-methoxybenzyloxycarbonyl)benzamidine, 0.8 g of anhydrous potassium carbonate, and 0.2 g of potassium iodide. The mixture was heated with stirring under reflux for 2 hours and then stripped of the solvent by distillation. The residue was washed thoroughly with water, then with ethanol to yield 3.5 g of colorless solid 3-benzoyl-4-(4-phthalimidomethylbenzyloxy)-N-(4-methoxybenzyloxycarbonyl)-benzamidine; m.p. 181°–182° C. (decomp.).

In a similar manner the following compounds were obtained:

3-Methoxy-4-(4-phthalimidomethylbenzyloxy)-N-(4-methoxybenzyloxycarbonyl)benzamidine; m.p. 168°–170° C. (decomp.).

4-Methoxy-3-(4-phthalimidomethylbenzyloxy)-N-(4-methoxybenzyloxycarbonyl)benzamidine; Rf=0.18, chloroform; m.p. 174°–176° C. (decomp.).

4-(4-Phthalimidomethylbenzyloxy)-N-(4-methoxybenzyloxycarbonyl)benzamidine; m.p. 175°–177° C. (decomp.).

3-Benzoyl-4-(2-chloro-4-phthalimidomethylbenzyloxy)-N-(4-methoxybenzyloxycarbonyl)benzamidine; m.p. 165.5°–168° C. (decomp.).

4-(2-Methoxy-4-phthalimidomethylbenzyloxy)-N-(4-methoxybenzyloxycarbonyl)benzamidine; m.p. 155°–158° C. (decomp.).

3-(2-Chloro-4-phthalimidomethylbenzyloxy)-4-methoxy-N-(4-methoxybenzyloxycarbonyl)benzamidine; m.p. 171°–172° C. (decomp.).

4-(2-Nitro-4-phthalimidomethylbenzyloxy)-N-(4-methoxybenzyloxycarbonyl)benzamidine; m.p. 175°–178° C. (decomp.).

EXAMPLE 26

To a suspension of 290 mg of 3-methoxy-4-(4-phthalimidomethylbenzyloxy)-N-(4-methoxybenzyloxycarbonyl)benzamidine in 5 ml of ethanol, was added 3 ml of hydrazine hydrate. The mixture was stirred at room temperature for 1.5 hours and filtered to collect the precipitate which is then washed with ethanol to yield 23 mg of colorless solid 4-(4-aminomethylbenzyloxy)-3-methoxy-N-aminobenzamidine. Further, the filtrate was evaporated to dryness and washed successively with aqueous ammonia, water, and ether to recover 97 mg of said benzamidine compound (120 mg in total).

IR $\nu_{max}^{KBr}$ cm$^{-1}$: 3400, 3290, 3120, 1623, 1580, 1505, 1410, 1365.

The above benzamidine compound was suspended in ethanol and mixed with an excess of methanesulfonic acid. The oily substance separated out of the mixture was crystallized from an ethanol-ether mixture to yield 170 mg of 4-(4-aminomethylbenzyloxy)-3-methoxy-N-aminobenzamidine dimethanesulfonate; m.p. 192°–193° C. (decomp.).

EXAMPLE 27

To a suspension of 1.7 g of 3-methoxy-4-(4-phthalimidomethylbenzyloxy)-N-(4-methoxybenzyloxycarbonyl)benzamidine in 20 ml of methanol, was added 11.8 ml of a methanol solution containing 40% of methylamine. The mixture was heated with stirring under reflux for 2 hours. The reaction mixture was stripped of the solvent and excess methylamine by distillation, then mixed with 10 ml of a methanol solution containing 16% of anhydrous hydrogen chloride, and again stripped of the solvent by distillation. The residue (yellow viscous oil) was recrystallized from an ethanol-acetonitrile mixture to yield 0.4 g of colorless solid 4-(4-aminomethylbenzyloxy)3-methoxy-N-methylbenzamidine dihydrochloride; m.p. 218°–220° C. (decomp.).

In a similar manner the following compounds were obtained:

3-(4-Aminomethylbenzyloxy)-4-methoxy-N-methylbenzamidine dihydrochloride; m.p. 201°–203° C. (decomp.).

4-(4-Aminomethylbenzyloxy)-N-methylbenzamidine dihydrochloride; ca. 256° C. (decomp.).

4-(4-Aminomethyl-2-methoxybenzyloxy)-N-methylbenzamidine dihydrochloride; m.p. 229°–232° C. (decomp.).

3-(4-Aminomethyl-2-chlorobenzyloxy)-4-methoxy-N-methylbenzamidine dihydrochloride; m.p. ca. 201° C. (decomp.).

4-(4-Aminomethylbenzyloxy)-3-α-methyliminobenzyl-N-methylbenzamidine trihydrochloride; m.p. ca. 203° C. (decomp.).

4-(4-Aminomethyl-2-nitrobenzyloxy)-N-methylbenzamidine dihydrochloride; m.p. ca. 216° C. (decomp.).

EXAMPLE 28

To a suspension of 1.4 g of 4-(2-chloro-4-phthalimidomethylbenzyloxy)-3-benzoyl-N-(4-methoxybenzyloxycarbonyl)benzamidine in 40 ml of methanol, was added 8 ml of a methanol solution containing 40% of methylamine. The mixture was heated with stirring under reflux for 5 hours and then stripped of the solvent and excess methylamine by distillation. The residue (yellow viscous oil) was mixed with 20 ml of 3N hydrochloric acid, heated under reflux for one hour, then cooled in ice, and filtered to collect the precipitate which was recrystallized from a methanol-acetonitrile mixture to yield 0.47 g of colorless solid 4-(4-aminomethyl-2-chlorobenzyloxy)-3-benzoyl-N-methylbenzamidine dihydrochloride. From the filtrate, there was obtained 0.16 g of the same compound (0.63 g in total); m.p. 182°–183° C. (decomp.).

In a similar manner, the following compound was obtained:

4-(4-Aminomethylbenzyloxy)-3-benzoyl-N-methylbenzamidine dihydrochloride; m.p. ca. 247° C. (decomp.).

EXAMPLE 29

To 25 ml of dried acetone, were added 1.0 g of 4-[3-(4-methoxybenzyloxycarbonylamino)-1-propenyl]benzyl chloride, 1.2 g of 3-benzoyl-4-hydroxy-N-(4-methoxybenzyloxycarbonyl)benzamidine, 0.4 g of anhydrous potassium carbonate, and 0.1 g of potassium iodide. The mixture was heated with stirring under reflux for 3.5 hours, then filtered from the insolubles, and stripped of the solvent by distillation. The residue was fractionated and purified by silica gel column chromatography (chloroform:methanol=50:1). The intended fractions (Rf=0.32) were collected and recrystallized from ethanol to yield 2.0 g of colorless solid 3-benzoyl-4-{4-[3-(4-methoxybenzyloxycarbonylamino)1-propenyl]benzyloxy}-N-(4-methoxybenzyloxycarbonyl)benzamidine; m.p. 118°–121° C.

In a similar manner the following compounds were obtained:

3-Benzoyl-4-{4-[3-(4-methoxybenzyloxycarbonylamino)propyl]benzyloxy}-N-(4-methoxybenzyloxycarbonyl)benzamidine; Rf=0.38, chloroform:methanol=50:1; colorless amorphous powder;
IR $\nu_{max}^{KBr}$ cm$^{-1}$: 3370, 2940, 1700, 1655, 1605, 1510, 1240.

3-Benzoyl-4-{4-[2-(4-methoxybenzyloxycarbonylamino)ethyl]benzyloxy}-N-(4-methoxybenzyloxycarbonyl)benzamidine; Rf=0.33, chloroform:methanol=50:1; colorless to pale yellow amorphous powder.
IR $\nu_{max}^{KBr}$ cm$^{-1}$: 3370, 2940, 1700, 1660, 1600, 1510, 1240.

3-{4-[3-(4-Methoxybenzyloxycarbonylamino)-1-propenyl]benzyloxy}-4-methoxy-N-(4-methoxybenzyloxycarbonyl)benzamidine; m.p. 129°–132° C.

4-{4-[3-(4-Methoxybenzyloxycarbonylamino)-1-propenyl]benzyloxy}-N-(4-methoxybenzyloxycarbonyl, benzamidine; m.p. 167°–169° C. (decomp.).

EXAMPLE 30

To 15 ml of acetic acid, was added 1.4 g of 3-benzoyl-4-{4-[3-(4-methoxybenzyloxycarbonylamino)-1-propenyl]benzyloxy}-N-(4-methoxybenzyloxycarbonyl)benzamidine. The mixture was heated under reflux for 5 minutes and then stripped of the solvent by distillation. The residue was washed with ether and mixed with 20 ml of a methanol solution containing 10% of anhydrous hydrogen chloride. The mixture was stirred at room temperature for 30 minutes and then stripped of the solvent by distillation. The residue was recrystallized from an ethanol-ether mixture to yield 0.8 g of 4-[4-(3-amino-1-propenyl)benzyloxy]-3-benzoylbenzamidine dihydrochloride; m.p. 168°–172° C. (decomp.).

In a similar manner, the following compounds were obtained:

4-[4-(3-Aminopropyl)benzyloxy]-3-benzoylbenzamidine dihydrochloride; m.p. 213°–215° C. (decomp.).

4-[4-(2-Aminoethyl)benzyloxy]-3-benzoylbenzamidine dihydrochloride; m.p. 224°–227° C. (decomp.).

EXAMPLE 31

To a mixture of 5 ml of methanol and 8 ml of chloroform, was added 357 mg of 3-benzoyl-4-{4-[3-(4-methoxybenzyloxycarbonylamino)-1-propenyl]benzyloxy}-N-(4-methoxybenzyloxycarbonyl)benzamidine followed by 5 ml of a methanol solution containing 40% of methylamine. The mixture was heated under reflux for 5.5 hours and then stripped of the solvent and excess methylamine. The residue was recrystallized from an ethanol-ether mixture to obtain a colorless solid. This solid was mixed with 5 ml of a methanol solution containing 10% of anhydrous hydrogen chloride, stirred at room temperature for 0.5 hour, and stripped of the solvent by distillation. The residue was recrystallized from an ethanol-acetonitrile mixture to yield 40 mg of pale green solid 4-[4-(3-amino-1-propenyl)benzyloxy]-3-benzoyl-N-methylbenzamidine dihydrochloride; m.p. 205°–207° C. (decomp.).

In a similar manner, the following compounds were obtained:

3-[4-(3-Amino-1-propenyl)benzyloxy]-4-methoxy-N-methylbenzamidine dihydrochloride; m.p. 209.5°–210° C. (decomp.).

4-[4-(3-Amino-1-propenyl)benzyloxy]-N-methylbenzamidine dihydrochloride; m.p. 183°–185° C. (decomp.).

PHARMACOLOGICAL EXPERIMENTS

1. Assessment of Cardiovascular Profile by Use of Blood-Perfused Heart Preparations.

Mongrel dogs of either sex weighting 7.5–10 kg were anesthetized with sodium pentobarbital (30 mg/kg, i.v.). Each animal was given an intravenous dose of sodium heparin (500 units/kg), thereafter, the heart was removed and placed in cold Tyrode solution. The isolated and cross-circulated right atrium and papillary muscle preparations were arranged for perfusion from a donor dog as follows. The donor dog was also anesthetized with sodium pentobarbital (30 mg/kg, i.v.); heparin (500 units/kg) was given intravenously immediately before the perfusion began.

(a) The isolated, blood-perfused papillary muscle preparation. The anterior septal artery was dissected and cannulated with polyethylene tubing. The tendinous end of the papillary muscle was connected to a strain-gauge transducer by a fine silk thread and the muscles were under about 2 g of resting tension. The papillary muscle preparation was electrically driven at a constant frequency of 120/min with rectangular pulses of 1–3 V and 5 msec duration. The preparation of the blood-perfused papillary muscle has been described in detail by Endoh and Hashimoto Am. J. Physiol, 218, 1459–1463 (1970).

(b) The isolated, blood-perfused right atrium preparation. The sinus node artery was cannulated at its origin in the right coronary artery. A right atrial electrogram was obtained from bipolar electrodes which were placed in close proximity to the sinoatrial node. The sinus rate was recorded by a cardiotachometer triggered by the right atrial electrogram. The details of the bloodperfused right atrium preparation have been described by Chiba et al. (Tohoku J. exp. Med., 107, 101–102 (1972) and Kubota and Hashimoto (Naunyn-Schmiedeberg's Arch. Pharmacol., 278, 135–150 (1973)).

Each preparation was perfused with the arterial blood from the carotid artery of the donor dog at a constant perfusion pressure of 100 mmHg by means of a peristaltic pump. The venous effluent from the preparations was collected in a reservoir and returned to the donor dog through the jugular vein.

Test compounds used in these experiments were dissolved in vehicle solution and were injected closearterially to the preparations. The effects of each compound on the developed tension and sinuo rate were evaluated as a percentage change in values determined before and after administration of the compound. In Table 1 are shown such changes in terms of the percentage increase after administration.

2. Assessment of the Cardiovascular Effect in Anesthetized Open-Chest Dogs

Mongrel dogs of either sex weighing 9–15 kg were anesthetized with sodium pentobarbital (30 mg/kg, i.v.). The heart was exposed by thoractomy by the left fifth intercostal incision under artificial respiration.

Aortic flow was measured by the probe of electromagnetic flowmeter placed around the ascending aorta. Myocardial contractility was measured by the maximal rate of rise of left ventricular pressure which was recorded from a needle inserted into the ventricular cavity.

The systemic blood pressure was measured with a pressure transducer by means of a polyethylene cannular inserted into the femoral artery. The heart rate was recorded by a cardiotrachometer triggered by R wave of electrocargiogram (Lead II). Test compounds were dissolved in vehicle solution and were injected into the femoral vein.

The effects of each compound on the cardiac contractility and aortic flow were evaluated as a percentage change in values determined before and after administration of the compound. In Table 2 are shown such changes in terms of the percentage increase after administration.

| Compound No. | Example No. | Test compound Compound |
|---|---|---|
| 1 | 9 | 4-[2-(4-Aminomethylphenyl)ethyl]-N—methylbenzamidine dihydrochloride |
| 2 | 9 | 4-[2-(4-Aminomethylphenyl)ethyl]-benzamidine dihydrochloride |
| 3 | 9 | 4-[2-(4-Aminomethyl-2-methoxyphenyl)ethyl]N—methylbenzamidine dihydrochloride |
| 4 | 9 | 4-[2-(4-Aminomethylphenyl)ethyl]-N—n-butylbenzamidine dihydrochloride |
| 5 | 9 | 4-[2-(4-Aminomethylphenyl)ethyl]-N—(2-phenylethyl)benzamidine dihydrochloride |
| 6 | 9 | 4-[2-(4-Aminomethylphenyl)ethyl]-N—[2-(2-pyridyl)ethyl]benzamidine trihydrochloride |
| 7 | 10 | 4-[2-(4-Aminomethylphenyl)ethenyl]-N—methylbenzamidine dihydrochloride |
| 8 | 22 | 4-(4-Aminomethylbenzyloxy)benzamidine diacetate |
| 9 | 22 | 4-(4-Aminomethylbenzyloxy)-3-benzoylbenzamidine acetate |
| 10 | 27 | 4-(4-Aminomethylbenzyloxy)-N—methylbenzamidine dihydrochloride |
| 11 | 30 | 4-[4-(3-Aminopropyl)benzyloxy]-3-benzoylbenzamidine dihydrochloride |
| 12 | 31 | 4-[4-(3-Amino-1-propenyl)benzyloxy]-3-benzoyl-N—methylbenzamidine dihydrochloride |
| 13 | 9 | N—Methyl-4-[2-(4-aminomethyl-2-nitrophenyl)ethyl]benzamidine dihydrochloride |
| 14 | 9 | N,N'—Dimethyl-4-[2-(4-aminomethylphenyl)ethyl]benzamidine dihydrobromide |
| 15 | 9 | 2-{4-[2-(4-Aminomethylphenyl)ethyl]phenyl}imidazoline dihydrochloride |
| 16 | 9 | 4-[2-(4-Aminomethylphenyl)ethyl]-N—methyl-3-nitrobenzamidine dihydrochloride |
| 17 | 9 | 4-[2-(4-Aminomethyl-2-methoxyphenyl)ethyl]-N,N'—dimethylbenzamidine dihydrochloride |
| 18 | 9 | 4-[2-(4-Aminomethyl-2-nitrophenyl)ethyl]-N,N'—dimethylbenzamidine dihydrochloride |
| 19 | 9 | 4-[2-(4-Aminomethyl-2-methoxyphenyl)ethyl]-N—[2-(2-pyridyl)ethyl]benzamidine trihydrochloride |
| 20 | 9 | 2-{4-[2-(4-Aminomethyl-2-methoxyphenyl)ethyl]phenyl}imidazoline dihydrochloride |

TABLE 1

| Compound No. | Dose (μg) | Papillary muscle preparation; % increase in developed tension | Right atrium preparation; % increase in sinus rate |
|---|---|---|---|
| 1 | 30 | 44.1 | 26.2 |
|   | 100 | 78.1 | 34.1 |
| 2 | 30 | 63.8 | 10.7 |
|   | 100 | 104.3 | 21.8 |
| 3 | 30 | 73.3 | 17.9 |
|   | 100 | 114.6 | 32.5 |
| 4 | 30 | 45.8 | 19.0 |
|   | 100 | 76.5 | 30.6 |
| 5 | 30 | 33.3 | 16.0 |
|   | 100 | 53.5 | 17.7 |
| 6 | 100 | 57.7 | 7.5 |
|   | 300 | 93.5 | 18.3 |
| 7 | 100 | 44.7 | 8.3 |
|   | 300 | 66.0 | 28.2 |
| 8 | 100 | 20.7 | 2.2 (−7.7) |
|   | 300 | 44.8 | 7.5 (−9.7) |
| 9 | 100 | 52.2 | 15.5 |
|   | 300 | 71.7 | 24.3 |
| 10 | 100 | 27.9 | 11.6 |
|   | 300 | 54.4 | 17.9 |
| 11 | 30 | 48.8 | 32.0 |
|   | 100 | 82.5 | 71.4 |
| 12 | 30 | 46.2 | 23.3 |
|   | 100 | 77.8 | 31.6 |
| 13 | 30 | 64.2 | 32.3 |
|   | 100 | 95.5 | 35.9 |
| 14 | 30 | 59.0 | 28.9 |
|   | 100 | 100.0 | 31.8 |
| 15 | 30 | 49.2 | 22.8 |
|   | 100 | 100.0 | 34.7 |
| 16 | 30 | 26.0 | 21.9 |
|   | 100 | 70.2 | 29.7 |
| 17 | 100 | 76.5 | 14.3 |
|   | 300 | 109.5 | 20.3 |
| 18 | 100 | 64.0 | 14.0 (−1.8) |
|   | 300 | 86.5 | 34.8 |
| 19 | 100 | 72.4 | 21.9 |
|   | 300 | 108.3 | 35.8 |
| 20 | 100 | 72.2 | 26.8 |
|   | 300 | 104.0 | 45.7 |

Note: In parentheses are shown % decrease.

TABLE 2

| Compound No. | Dose (mg/kg) | Increase in cardiac contractility (%) | Increase in aortic flow (%) |
|---|---|---|---|
| 1 | 0.1 | 42.1 | 30.4 |
|   | 0.3 | 57.5 | 38.8 |
| 2 | 0.03 | 7.1 | 5.0 |
|   | 0.1 | 25.0 | 16.1 |
| 3 | 0.01 | 14.0 | 4.1 |
|   | 0.03 | 24.6 | 21.7 |
| 4 | 0.1 | 26.1 | 20.0 |
|   | 0.3 | 52.9 (−3.4) | 50.0 |
| 5 | 0.1 | 12.9 | 5.0 |
|   | 0.3 | 38.9 | 19.2 |
| 6 | 0.03 | 5.2 | 1.8 |

TABLE 2-continued

| Compound No. | Dose (mg/kg) | Increase in cardiac contractility (%) | Increase in aortic flow (%) |
|---|---|---|---|
|  | 0.1 | 18.0 | 6.5 |
| 7 | 0.1 | 3.1 | 4.2 |
|  | 0.3 | 16.7 | 13.8 |
| 8 | 0.1 | 0 | 6.1 |
|  | 0.3 | 16.7 | 9.5 |
| 9 | 0.1 | 12.5 (−7.1) | 3.9 (−7.9) |
| 10 | 0.3 | 8.7 | 2.5 |
| 11 | 0.1 | 14.3 | 7.5 |
| 12 | 0.03 | 18.8 | 6.1 |
|  | 0.1 | 40.0 | 8.7 |
| 13 | 0.03 | 29.0 | 5.7 |
|  | 0.1 | 66.7 | 12.1 |
| 14 | 0.1 | 30.0 | 8.7 |
|  | 0.3 | 47.5 (−6.8) | 32.7 (−16.3) |
| 15 | 0.1 | 25.0 | 5.9 |
|  | 0.3 | 56.5 | 10.0 |
| 16 | 0.1 | 32.0 | 9.0 |
|  | 0.3 | 69.4 | 16.3 (−7.0) |
| 17 | 0.03 | 13.5 | 4.7 |
|  | 0.1 | 76.5 | 17.0 |
| 18 | 0.1 | 59.3 | 14.3 |
|  | 0.3 | 155.2 | 23.7 (−5.3) |
| 19 | 0.1 | 20.0 | 9.2 |
|  | 0.3 | 128.6 (−7.1) | 11.9 (−1.2) |
| 20 | 0.03 | 78.6 (−7.8) | 7.9 (−1.1) |

Note: In parentheses are shown % decrease.

Toxicity

The toxicity ($LD_{50}$) of the compounds of this invention were as shown in the following table.

| Compound No. | $LD_{50}$ in mg/kg; mouse; I.V. |
|---|---|
| 2 | 40.0 |
| 5 | 57.7 |
| 8 | 57.7 |

Examples of pharmaceutical preparations of the present compounds are described below. Example of pharmaceutical preparation.

(1) Capsule:
| | |
|---|---|
| Compound of general formula [I] | 100.0 mg |
| Corn starch | 100.0 |
| Microcrystalline cellulose | 37.0 |
| Talc | 13.0 |
| Total | 250.0 |

(2) Fine granule:
| | |
|---|---|
| Compound of general formula [I] | 50.0 mg |
| Lactose | 249.0 |
| Mannitol | 75.0 |
| Corn starch | 110.0 |
| Hydroxypropylcellulose | 16.0 |
| Total | 500.0 |

(3) Injection:
| | |
|---|---|
| Compound of general formula [I] | 5.0 mg |
| Water for injection | 2 ml |
| Make up to a parenteral injection in a customary manner. | |

(4) Tablet:
| | |
|---|---|
| Compound of general formula [I] | 100.0 mg |
| Lactose | 62.0 |
| Corn starch | 27.0 |
| Hydroxypropylcellulose | 6.0 |
| Stearic acid | 3.0 |
| Talc | 2.0 |
| Total | 200.0 |

What is claimed is:

1. A compound represented by the following formula [I] or a salt thereof:

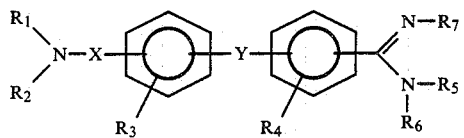

wherein $R_1$ and $R_2$, which may be the same or different, represent each a hydrogen atom or a lower alkyl group, or $R_1$ and $R_2$ together with an intermediary carbon atom and/or hetero atom may form a ring; X represents

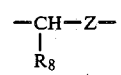

(wherein $R_8$ represents a hydrogen atom, a lower alkyl group, or —$CH_2COOR_9$, where $R_9$ represents a hydrogen atom or a lower alkyl group; Z represents a single bond, —$CH_2$—, —$CH_2CH_2$—, or —CH=CH—); $R_3$ represents a hydrogen or chlorine atom, methoxy group, nitro group, or amino group; Y represents —$CH_2CH_2$—, —CH=CH—, —$CH_2O$—, or —$OCH_2$—; $R_4$ represents a hydrogen atom, methoxy group, benzoyl group, nitro group, or amino group; and $R_5$, $R_6$ and $R_7$, which may be the same or different, represent each a hydrogen atom, lower alkyl group, cycloalkyl group, aralkyl group, substituted alkyl group, substituted aralkyl group, or amino group, or $R_5$ and $R_7$ may form an imidazoline ring or a methyl substituted imidazoline ring.

2. A cardiotonic agent comprising as active ingredient an amidine derivative represented by the following formula [I] or a salt thereof:

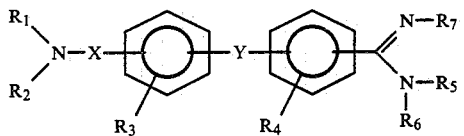

wherein $R_1$ and $R_2$, which may be the same or different, represent each a hydrogen atom or a lower alkyl group, or $R_1$ and $R_2$ together with an intermediary carbon atom and/or hetero atom may form a ring; X represents

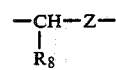

(wherein $R_8$ represents a hydrogen atom, or a lower alkyl group; Z represents a single bond, —$CH_2$—, —$CH_2CH_2$—, or —CH=CH—); $R_3$ represents a hydrogen or chlorine atom, methoxy group, nitro group, or amino group; Y represents —$CH_2CH_2$—, —CH=CH—, —$CH_2O$—, or —$OCH_2$—; $R_4$ represents a hydrogen atom, methoxy group, benzoyl group, nitro group, or amino group; and $R_5$, $R_6$ and $R_7$, which may be the same or different, represent each a hydrogen atom, lower alkyl group, cycloalkyl group, aralkyl group, substituted alkyl group, substituted aralkyl group, or amino group, or $R_5$ and R7 may form an imidazoline ring or a methyl substituted imidazoline ring, in association with a pharmaceutically acceptable carrier.

* * * * *